(12) United States Patent
Millis et al.

(10) Patent No.: US 7,897,327 B2
(45) Date of Patent: Mar. 1, 2011

(54) METHOD AND APPARATUS FOR PRESSURE CONTROL FOR MAINTAINING VIABILITY OF ORGANS

(75) Inventors: Roger Millis, West Jordan, UT (US); John Foley, Salt Lake City, UT (US); Doug Schein, Chicago, IL (US); John Brassil, North Brook, IL (US)

(73) Assignee: Organ Recovery Systems, Inc., Des Plaines, IL (US)

( * ) Notice: Subject to any disclaimer, the term of this patent is extended or adjusted under 35 U.S.C. 154(b) by 773 days.

(21) Appl. No.: 10/449,513

(22) Filed: Jun. 2, 2003

(65) Prior Publication Data

US 2004/0241634 A1 Dec. 2, 2004

(51) Int. Cl.
*A01N 1/00* (2006.01)
*A01N 1/02* (2006.01)

(52) U.S. Cl. .................. 435/1.2; 435/284.1; 417/19
(58) Field of Classification Search .................. 435/1.2, 435/284.1; 417/7, 14, 19, 38
See application file for complete search history.

(56) References Cited

U.S. PATENT DOCUMENTS

| | | | |
|---|---|---|---|
| 3,639,084 A | 2/1972 | Goldhaber |
| 3,738,914 A | 6/1973 | Thorne et al. |
| 3,878,567 A | 4/1975 | Purdy |
| 3,892,628 A | 7/1975 | Thorne et al. |
| 3,995,444 A | 12/1976 | Clark et al. |
| 4,231,354 A | 11/1980 | Kurtz et al. |
| 4,629,686 A | 12/1986 | Gruenberg |
| 4,745,759 A | 5/1988 | Bauer et al. |
| 5,051,352 A | 9/1991 | Martindale et al. |
| 5,141,847 A | 8/1992 | Sugimachi et al. |
| 5,149,321 A | 9/1992 | Klatz et al. |
| 5,157,930 A | 10/1992 | McGhee et al. |

(Continued)

FOREIGN PATENT DOCUMENTS

WO    WO 9114364  A1  * 10/1991

(Continued)

OTHER PUBLICATIONS

U.S. Appl. No. 09/162,128, filed Sep. 29, 1998, Donald R. Owen et al.

(Continued)

*Primary Examiner*—William H Beisner
*Assistant Examiner*—Michael Hobbs
(74) *Attorney, Agent, or Firm*—Oliff & Berridge, PLC

(57) ABSTRACT

A method for controlling a pump for delivery of liquid to an organ over a series of fixed-length time intervals f, each interval f comprising a time $t_1$ and a time $t_2$ wherein $t_1+t_2$ equals the length of interval f. The method comprises allowing output pressure of the pump to decrease over time $t_1$, increasing output pressure of the pump over time $t_2$, comparing achieved pump output pressure to a predetermined pressure at about the end of interval f, and at least one of (i) adjusting $t_1$ and $t_2$ if necessary so the predetermined pressure is approximated by the output pressure at the end of the next interval f, and (ii) adjusting a rate of change of the output pressure during at least one of $t_1$ and $t_2$ if necessary so the predetermined pressure is approximated by the output pressure at the end of the next interval f.

29 Claims, 14 Drawing Sheets

U.S. PATENT DOCUMENTS

| | | | |
|---|---|---|---|
| 5,217,860 A | 6/1993 | Fahy et al. | |
| 5,285,657 A | 2/1994 | Bacchi et al. | |
| 5,326,706 A | 7/1994 | Yland et al. | |
| 5,338,662 A | 8/1994 | Sadri | |
| 5,395,314 A | 3/1995 | Klatz et al. | |
| 5,472,876 A | 12/1995 | Fahy | |
| 5,476,763 A | 12/1995 | Bacchi et al. | |
| 5,494,822 A | 2/1996 | Sadri | |
| 5,584,804 A | 12/1996 | Klatz et al. | |
| 5,586,438 A | 12/1996 | Fahy | |
| 5,709,654 A | 1/1998 | Klatz et al. | |
| 5,752,929 A | 5/1998 | Klatz et al. | |
| 5,827,222 A | 10/1998 | Klatz et al. | |
| 5,933,320 A * | 8/1999 | Malhi | 361/680 |
| 6,014,864 A | 1/2000 | Owen | |
| 6,046,046 A * | 4/2000 | Hassanein | 435/284.1 |
| 6,209,343 B1 | 4/2001 | Owen | |
| 6,492,103 B1 | 12/2002 | Taylor | |
| 6,673,594 B1 * | 1/2004 | Owen et al. | 435/284.1 |
| 2003/0045772 A1 * | 3/2003 | Reich et al. | 600/18 |
| 2003/0103035 A1 * | 6/2003 | Watanabe et al. | 345/156 |

FOREIGN PATENT DOCUMENTS

WO    WO 02/26034 A2    4/2002

OTHER PUBLICATIONS

U.S. Appl. No. 09/537,180, filed Mar. 29, 2000, Donald R. Owen et al.

U.S. Appl. No. 60/459,986, filed Apr. 4, 2003, David W. Wright et al.

U.S. Appl. No. 60/459,981, filed Apr. 4, 2003, David W. Wright et al.

U.S. Appl. No. 60/460,875, filed Apr. 8, 2003, Douglas A. Schein et al.

U.S. Appl. No. 09/645,525, filed Aug. 25, 2000, Donald R. Owen et al.

* cited by examiner

METHOD AND APPARATUS FOR PRESSURE CONTROL FOR MAINTAINING VIABILITY OF ORGANS

BACKGROUND OF THE INVENTION

1. Field of the Invention

The invention relates to apparatus and methods for perfusing, in a defined and controlled manner, one or more organs, tissues or the like (hereinafter generally referred to as organs) to sustain, maintain and/or improve the viability of the organ(s).

2. Description of Related Art

Preservation of organs by machine perfusion has been accomplished at hypothermic temperatures with crystalloid perfusates and without oxygenation. See, for example, U.S. Pat. Nos. 5,149,321, 5,395,314, 5,584,804, 5,709,654, 5,752,929 and 5,827,222 to Klatz et al., which are hereby incorporated by reference. Hypothermic temperatures provide a decrease in organ metabolism, lower energy requirements, delay depletion of high energy phosphate reserves and accumulation of lactic acid and retard morphological and functional deterioration associated with disruption of blood supply.

Ideally organs would be procured in a manner that limits their warm ischemia time to essentially zero. Unfortunately, in reality, many organs, especially from non-beating heart donors, are procured after extended warm ischemia time periods (i.e., 45 minutes or more). The machine perfusion of these organs at low temperature has demonstrated significant improvement (Transpl Int 1996 Daemen). Further, prior art teaches that the low temperature machine perfusion of organs is preferred at low pressures (Transpl. Int 1996 Yland) with roller or diaphragm pumps delivering the perfusate at a controlled pressure. Numerous control circuits and pumping configurations have been utilized to achieve this objective and to machine perfuse organs in general. See, for example, U.S. Pat Nos. 5,338,662 and 5,494,822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thorne et al.; U.S. Pat. Nos. 5,285,657 and 5,476,763 to Bacchi et al.; U.S. Pat. No. 5,157,930 to McGhee et al.; and U.S. Pat. No. 5,141,847 to Sugimachi et al. However, the use of such pumps for machine perfusion of organs may increase the risk of under or over-pressurization of the organ. High pressure perfusion (e.g., above about 60 mm Hg), for example, can wash off the vascular endothelial lining of the organ and in general damages organ tissue, in particular at hypothermic temperatures where the organ does not have neurological or endocrinal connections to protect itself by dilating its vasculature under high pressure. Lower than needed pressure perfusion may result in organ failure.

Therefore, a need exists for a method and apparatus for perfusing an organ at a user or predefined pressure which takes into account organ resistance (i.e., pressure/flow) to avoid damage to the organ and to maintain the organ's viability.

SUMMARY OF THE INVENTION

The present invention focuses on avoiding damage to an organ during perfusion while monitoring, sustaining and/or restoring the viability of the organ and preserving the organ for transplant, storage and/or transport. More particularly, the organ perfusion apparatus and method according to the present invention are directed to perfusing an organ at a user or predefined pressure or pressure wave, to monitor, sustain and/or restore the viability of the organ and/or for transporting and/or storing the organ.

In perfusion, gross organ perfusion pressure may be provided by a pneumatically pressurized medical fluid reservoir controlled by a computer. The computer can respond to a sensor or similar device, for example, disposed in an end of tubing placed in the organ. The computer may be used in combination with a stepping motor/cam valve or pinch valve which provides for perfusion pressure fine tuning, prevents overpressurization and/or provides emergency flow cut-off. Alternatively, the organ may be perfused directly from a computer controlled pump, such as a roller pump or a peristaltic pump, with proper pump control and/or sufficiently fail-safe controllers to prevent overpressurization of the organ, especially as a result of a system malfunction. Substantially eliminating overpressurization prevents and/or reduces damage to the vascular endothelial lining and to the organ tissue in general.

Roller and peristaltic pumps produce pressure spikes which appear due to the rollers in the pumps. These spikes may be removed by having a motor which increases and decreases running speed according to the location of the roller head or the continuous feedback of a pressure sensor. A mechanical damper, typically an air pocket, is typically used to absorb the pressure spikes. Although known roller and peristaltic pumps may reduce the pressure spikes, however, the introduction of pressure spikes into the fluid flow according to embodiments of the present invention advantageously enables the maintaining of the pressure of fluid flowing into an organ between a user or pre-defined specified systolic pressure and a diastolic pressure of the organ.

According to one embodiment of the present invention, the introduction of pressure spikes resulting in the aforementioned benefits may be achieved by a method of delivering a liquid to an organ or tissue by means of a pump.

Exemplary embodiments of the invention may be used for various organs, such as the kidneys, and may be adapted to more complex organs, such as the liver, having multiple vasculature structures, for example, the hepatic and portal vasculatures of the liver.

An organ diagnostic apparatus may also be provided to produce diagnostic data such as an organ viability index. The organ diagnostic apparatus includes features of an organ perfusion apparatus, such as sensors and temperature controllers, as well as cassette interface features, and provides analysis of input and output fluids in a perfusion system. Typically, the organ diagnostic apparatus is a simplified perfusion apparatus providing diagnostic data in a single pass, in-line perfusion.

Embodiments of the invention also provide an organ cassette which allows an organ to be easily and safely moved between apparatus for perfusing, storing, analyzing and/or transporting the organ. The organ cassette may be configured to provide uninterrupted sterile conditions and efficient heat transfer during transport, recovery, analysis and storage, including transition between the transporter, perfusion apparatus and organ diagnostic apparatus, and/or other apparatus.

Embodiments of this invention also provide an organ transporter which allows for transportation of an organ, particularly over long distances. The organ transporter may include features of an organ perfusion apparatus, such as sensors and temperature controllers, as well as cassette interface features.

Embodiments of this perfusion apparatus, transporter, cassette, and organ diagnostic apparatus may be networked to permit remote management, tracking and monitoring of the location and therapeutic and diagnostic parameters of the organ or organs being stored or transported. The information systems may be used to compile historical data of organ transport and storage, and provide cross-referencing with hospital and United Network for Organ Sharing (UNOS) data on the donor and recipient. The systems may also provide outcome data to allow for ready research of perfusion parameters and transplant outcomes.

These and other features and advantages of this invention are described in, or are apparent from, the following detailed description of various exemplary embodiments of systems and methods according to this invention.

BRIEF DESCRIPTION OF THE DRAWINGS

The above and other aspects and advantages of the invention will become apparent from the following detailed description of embodiments when taken in conjunction with the accompanying drawings, in which.

DETAILED DESCRIPTION OF PREFERRED EMBODIMENTS

Figure 1:
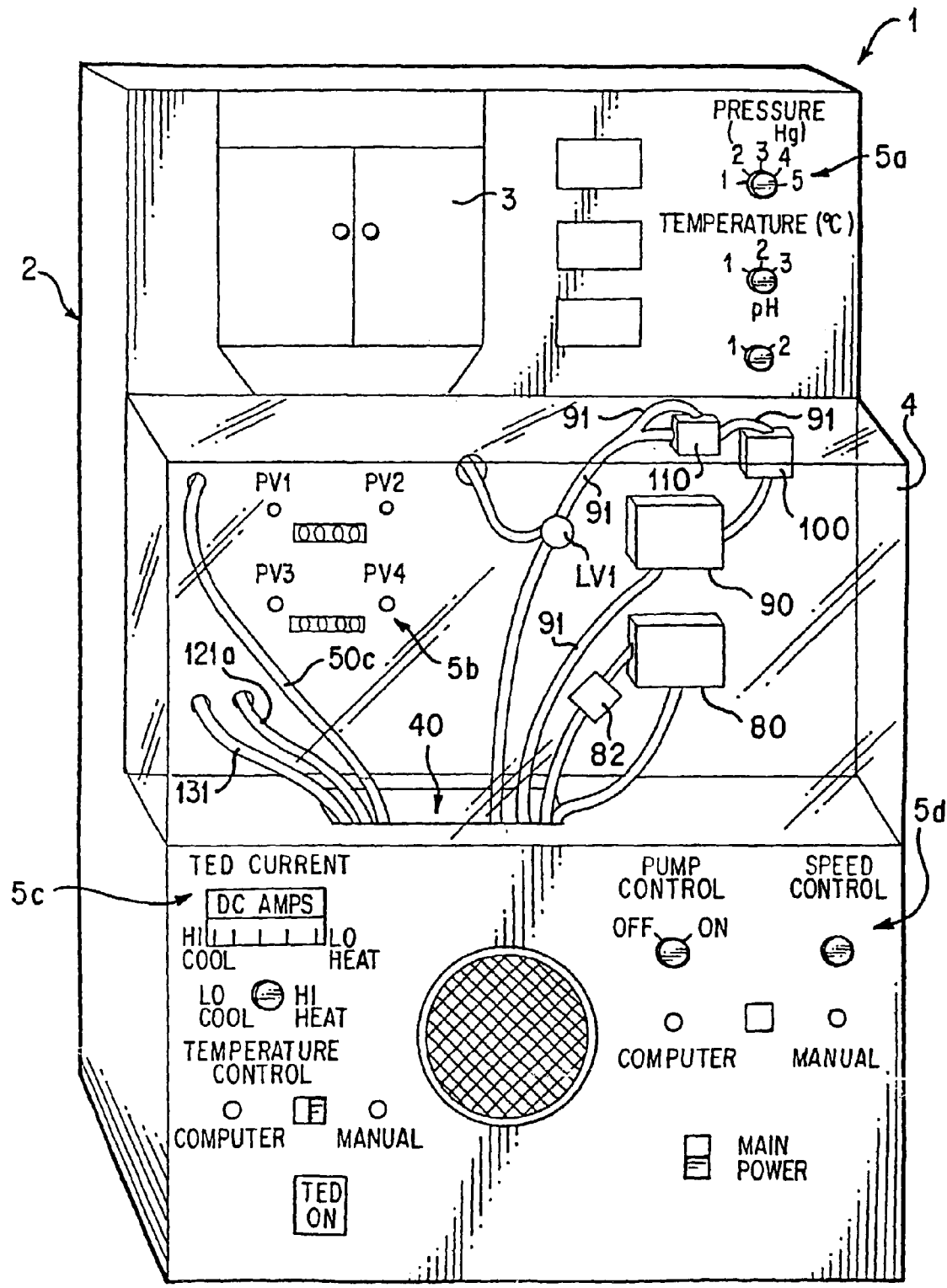
FIG. 1 is an organ perfusion apparatus according to the invention.

For a general understanding of the features of the invention, reference is made to the drawings. In the drawings, like reference numerals have been used throughout to designate like elements.

The invention is described herein largely in the context of apparatus and methods involved in transport, storage, perfusion and diagnosis of tissues and organs. However, the inventive apparatus and methods have many other applications, and thus the various inventive structures, devices, apparatus and methods described herein should not be construed to be limited to particular contexts of use. Various features of the disclosed invention are particularly suitable for use in the context of, and in conjunction and/or connection with the features of the apparatus and methods disclosed in U.S. patent application Ser. No. 09/162,128, U.S. Pat. No. 6,977,140, Provisional Patent Applications Nos. 60/459,986, 60/459,981, and 60/460,875, and U.S. Pat. No. 6,673,594, the entire disclosures of which are hereby incorporated by reference.

Figure 2:
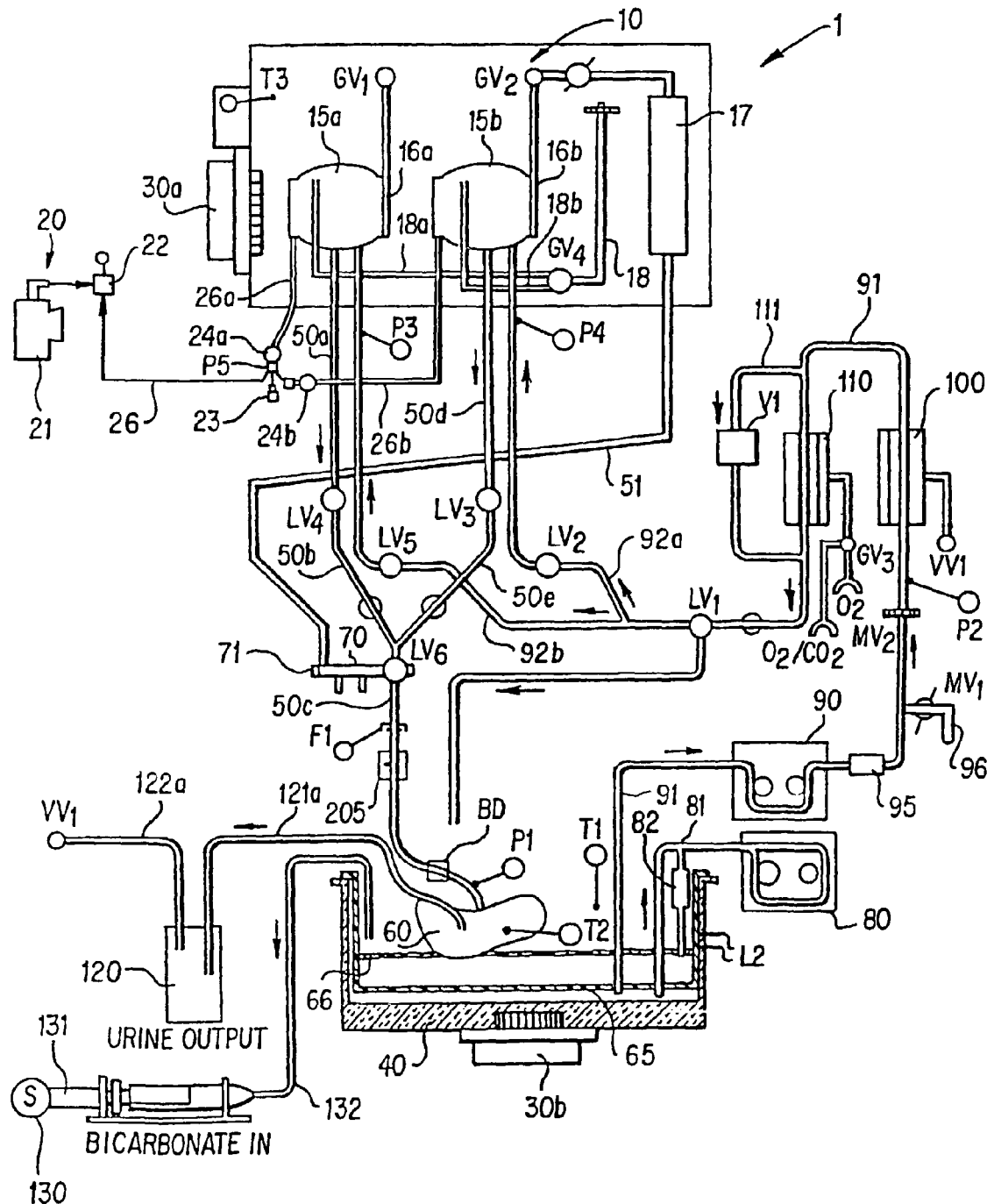
FIG. 2 is a schematic diagram of an apparatus of FIG. 1.
Figure 3:
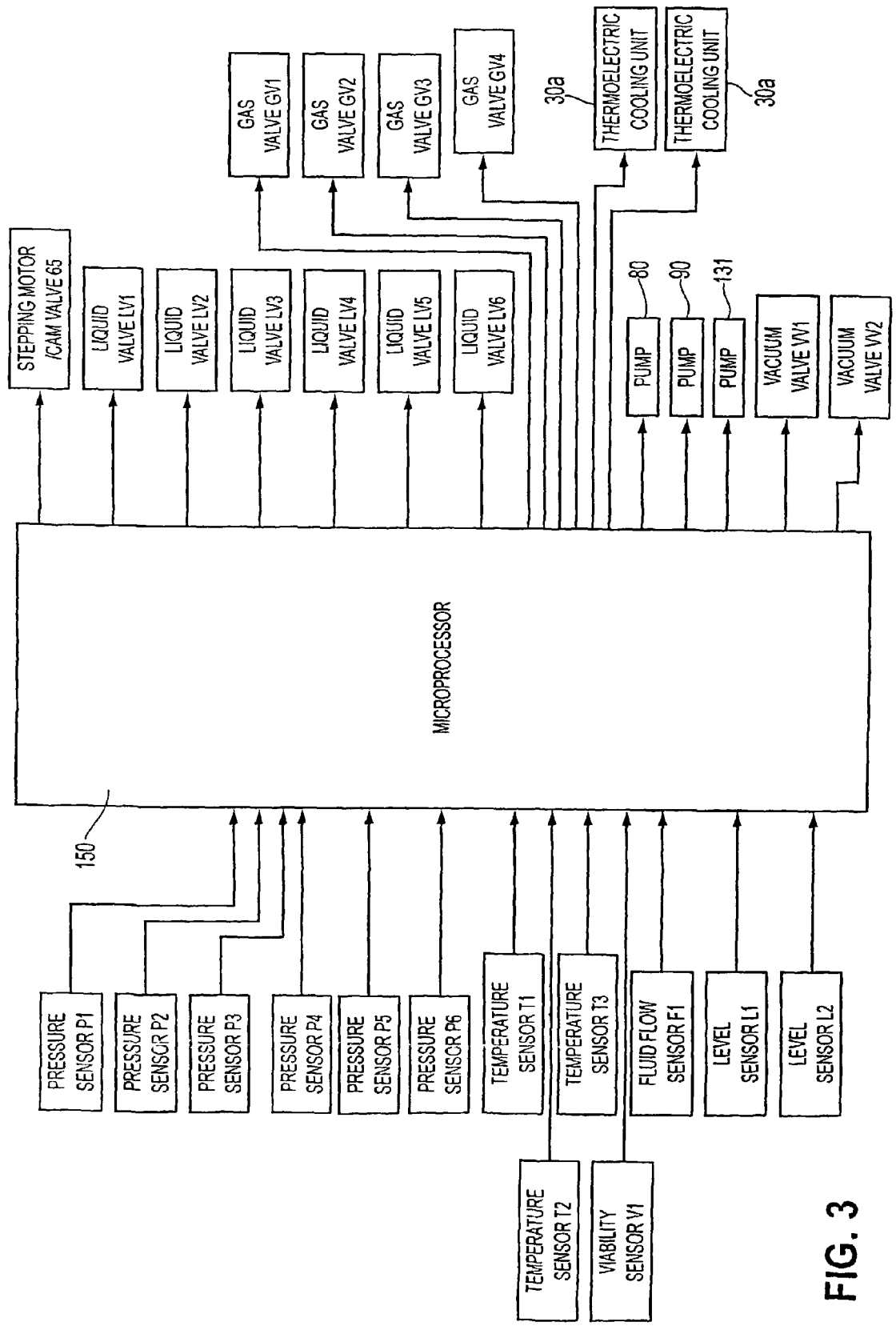
FIG. 3 is a diagram of a microprocessor controller which may be integrated with the apparatus of FIG. 2, the organ cassettes of FIG. 4D, and/or the organ transporter of FIG. 9.

FIG. 1 shows an organ perfusion apparatus 1 according to embodiments of the invention. FIG. 2 is a schematic illustration of the apparatus of FIG. 1. The apparatus 1 is preferably at least partially microprocessor controlled, and pneumatically actuated. A microprocessor 150 connection to the sensors, valves, thermoelectric units and pumps of the apparatus 1 is schematically shown in FIG. 3. Microprocessor 150 and apparatus 1 may be configured to and are preferably capable of further being connected to a computer network to provide data sharing, for example across a local area network or across the Internet.

The organ perfusion apparatus 1 is preferably capable of perfusing one or more organs simultaneously, at both normothermic and hypothermic temperatures (hereinafter, normothermic and hypothermic perfusion modes). All medical fluid contact surfaces are preferably formed of or coated with materials compatible with the medical fluid used, more preferably non-thrombogenic materials. As shown in FIG. 1, the apparatus 1 may include a housing 2 which includes front cover 4, which is preferably translucent, and a reservoir access door 3. The apparatus preferably has one or more control and display areas 5a, 5b, 5c, 5d for monitoring and controlling perfusion.

As schematically shown in FIG. 2, enclosed within the housing 2 is a reservoir 10 which preferably includes three reservoir tanks 15a, 15b, 17. Two of the reservoir tanks 15a, 15b are preferably standard one liter infusion bags, each with a respective pressure cuff 16a, 16b. A pressure source 20 can be provided for pressurizing the pressure cuffs 16a, 16b. The pressure source 20 is preferably pneumatic and may be an on board compressor unit 21 supplying at least 10 LPM external cuff activation via gas tubes 26, 26a, 26b, as shown in FIG. 2. The invention, however, is not limited to use of an on board compressor unit as any adequate pressure source can be employed, for example, a compressed gas (e.g., air, $CO_2$, oxygen, nitrogen, etc.) tank (not shown) preferably with a tank volume of 1.5 liters at 100 psi or greater for internal pressurization. Alternatively, an internally pressurized reservoir tank (not shown) may be used. Reservoir tanks 15a, 15b, 17 may, in embodiments, be bottles or other suitably rigid reservoirs that can supply perfusate by gravity or can be pressurized by compressed gas.

Gas valves 22-23 may be provided on the gas tube 26 to allow for control of the pressure provided by the onboard compressor unit 21. Anti-back flow valves 24a, 24b may be provided respectively on the gas tubes 26a, 26b. Pressure sensors P1, P2, P3, P4, P5, and P6 may be provided to relay pressure conditions detected to the microprocessor 150, shown in FIG. 3. Perfusion, diagnostic and/or transporter apparatus may be provided with sensors to monitor perfusion fluid pressure and flow in the particular apparatus to detect faults in the particular apparatus, such as pressure elevated above a suitable level for maintenance of the organ. Gas valves $GV_1$ and $GV_2$ may be provided to release pressure from the cuffs 16a, 16b. One or both of gas valves $GV_1$ and $GV_2$ may be vented to the atmosphere. Gas valve $GV_4$ in communication with reservoir tanks 15a, 15b via tubing 18a, 18b may be provided to vent air from the reservoir tanks 15a, 15b through tubing 18. Tubing 18, 18a, 18b, 26, 26a and/or 26b may be configured with filters and/or check valves to prevent biological materials from entering the tubing or from proceeding further along the fluid path. The check valves and/or filters may be used to prevent biological materials from leaving one organ perfusion tubeset and being transferred to the tubeset of a subsequent organ in a multiple organ perfusion configuration. The check valves and/or filters may also be used to prevent biological materials, such as bacteria and viruses, from being transferred from organ to organ in subsequent uses of the perfusion apparatus in the event that such biological materials remain in the perfusion apparatus after use. The check valves and/or filters may be provided to prevent contamination problems associated with reflux in the gas and/or vent lines. For example, the valves may be configured as anti-reflux valves to prevent reflux. The third reservoir tank 17 is preferably pressurized by pressure released from one of the pressure cuffs via gas valve $GV_2$.

The medical fluid may be a natural fluid such as blood, but is preferably synthetic and may, for example, be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. An oxygenated (e.g., cross-linked hemoglobin-based bicarbonate) solution is preferred for a normothermic mode while a non-oxygenated (e.g., simple crystalloid solution preferably augmented with antioxidants) solution is preferred for a hypothermic mode. The specific medical fluids used in both the normothermic and hypothermic modes may be designed or selected to reduce or prevent the washing away of or damage to the vascular endothelial lining of the organ. For a hypothermic perfusion mode, as well as for flush and/or static storage, a preferred solution is the solution disclosed in U.S. Pat. No. 6,492,103, the entire disclosure of which is incorporated herein by reference. Examples of additives which may be used in perfusion solutions for the present invention are also disclosed in U.S. Pat. No. 6,046,046 to Hassanein, the entire disclosure of which is incorporated by reference. Of course, other suitable solutions and materials may be used, as is known in the art.

The medical fluid within reservoir 10 is preferably brought to a predetermined temperature by a first thermoelectric unit 30a in heat transfer communication with the reservoir 10. A temperature sensor T3 relays the temperature within the reservoir 10 to the microprocessor 150, which adjusts the thermoelectric unit 30a to maintain a desired temperature within the reservoir 10 and/or displays the temperature on a control and display areas 5a for manual adjustment. Alternatively or in addition, and preferably where the organ perfusion device is going to be transported, the medical fluid within the hypothermic perfusion fluid reservoir can be cooled utilizing a cryogenic fluid heat exchanger apparatus such as that disclosed in filed U.S. Pat. No. 6,014,864, which is hereby incorporated by reference.

Figure 4A:
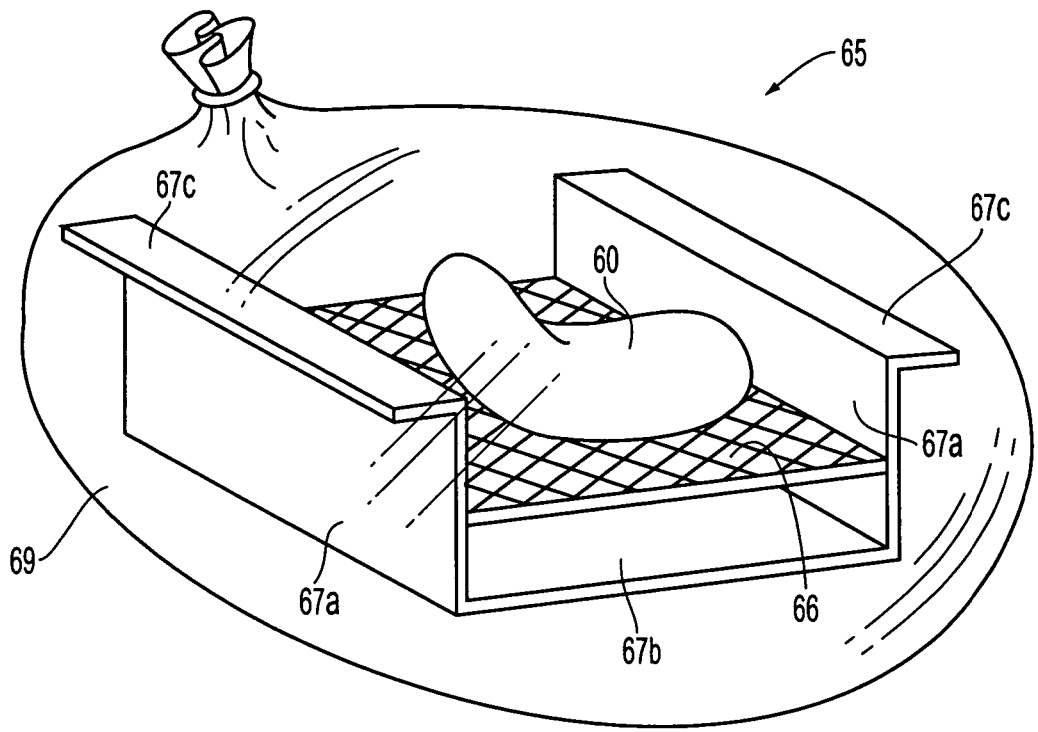
FIGS. 4A-4D show perspective views of various embodiments of an organ cassette according to the invention.
Figure 4B:
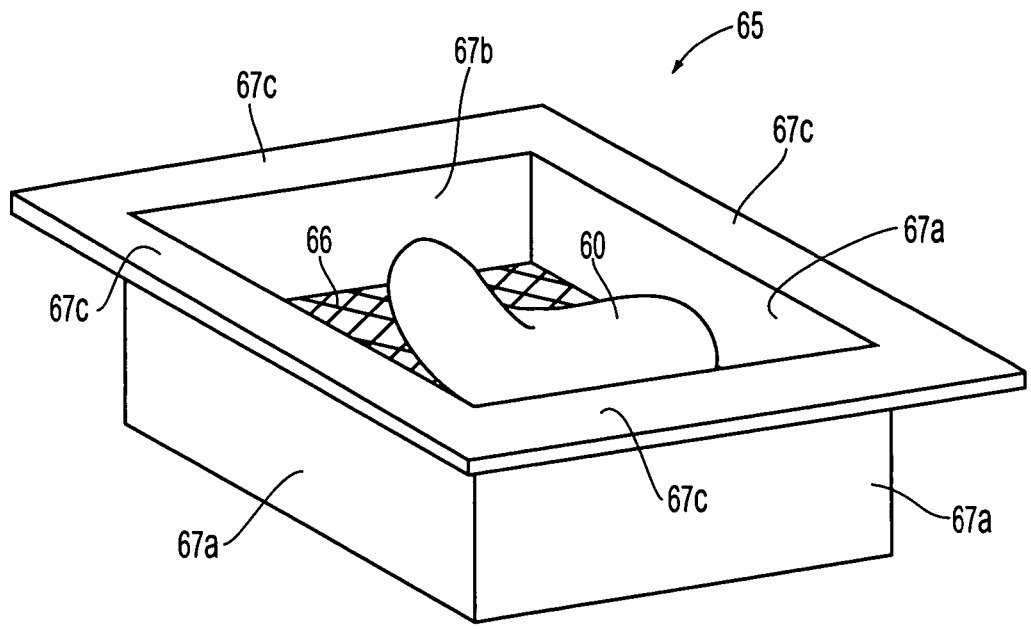
Figure 4D:
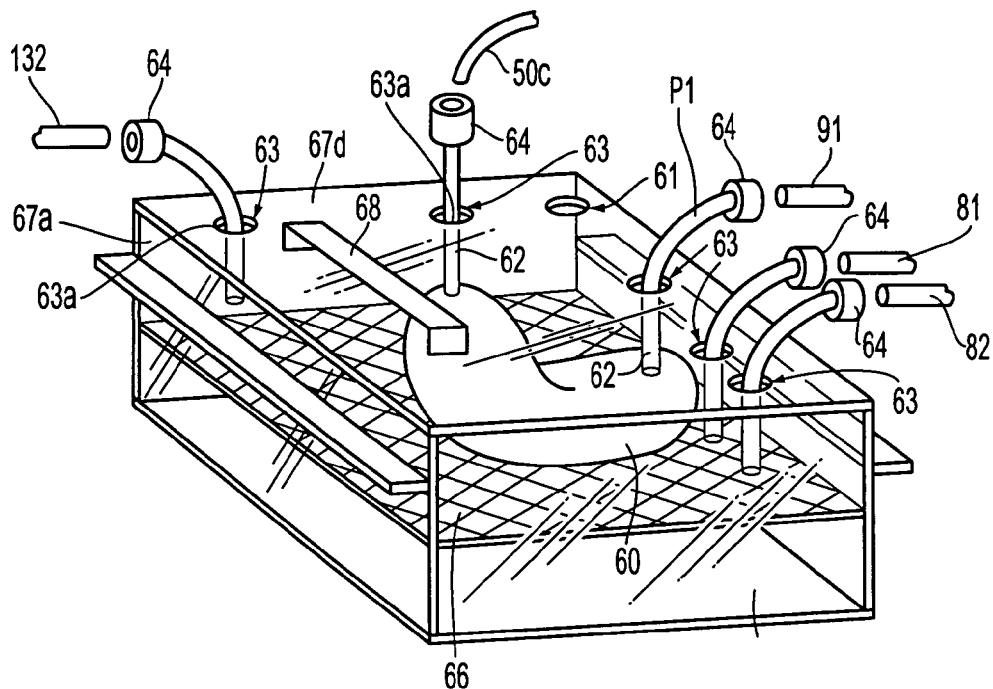
Figure 4C:
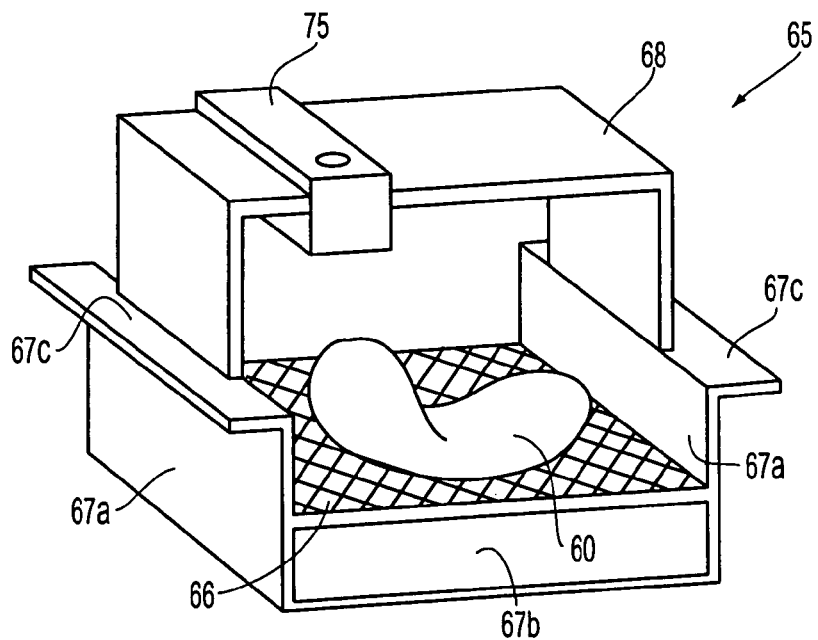
Figure 5:
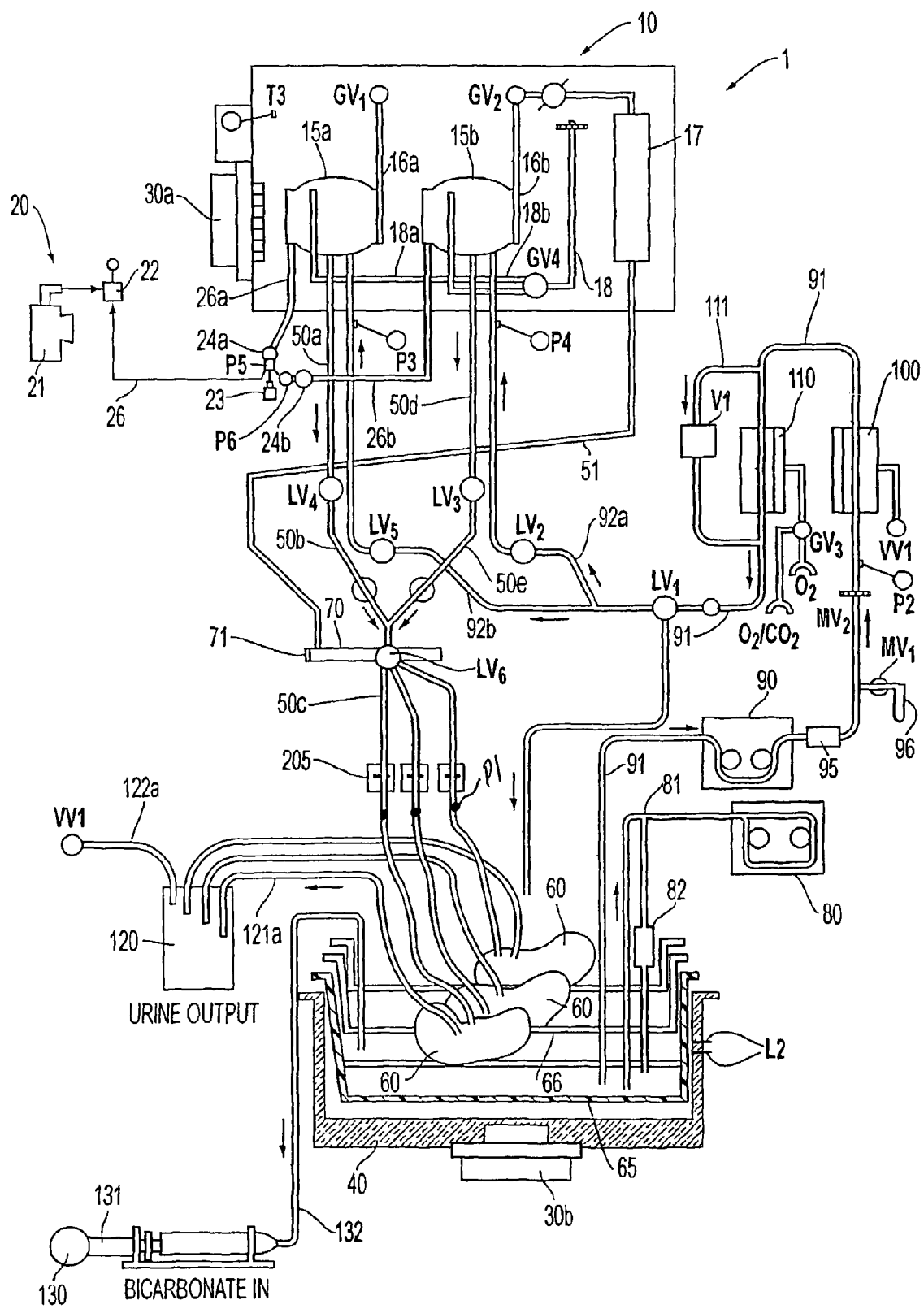
FIG. 5 is a schematic diagram of an organ perfusion apparatus configured to simultaneously perfuse multiple organs.

An organ chamber 40 is provided which supports a cassette 65, as shown in FIG. 2, which holds an organ to be perfused, or a plurality of cassettes 65, as shown in FIG. 5, preferably disposed one adjacent the other. Various embodiments of the cassette 65 are shown in FIGS. 4A-4D. The cassette 65 is preferably formed of a material that is light but durable so that the cassette 65 is highly portable. The material may also be transparent to allow visual inspection of the organ.

FIG. 4A shows a cassette 65 which holds an organ 60 to be perfused. Various embodiments of such a cassette 65 are shown in FIGS. 4A-4D, 6A, 6B, 10 and 12. The cassette 65 is preferably formed of a material that is light but durable so that the cassette 65 is highly portable. The material may also be transparent to allow visual inspection of the organ.

Preferably the cassette 65 includes side walls 67a, a bottom wall 67b and an organ supporting surface 66, which is preferably formed of a porous, perforated or mesh material to allow fluids to pass therethrough. The cassette 65 may also include a top 67d and may be provided with an opening(s) 63 for tubing (see, for example, FIG. 4D). The opening(s) 63 may include seals 63a (e.g., septum seals or o-ring seals) and optionally be provided with plugs (not shown) to prevent contamination of the organ and maintain a sterile environment. Also, cassette 65 may be provided with a closeable and/or filtered vent 61 (see, for example, FIG. 4D). Additionally, the cassette 65 may be provided with tubing for connection to an organ and/or to remove medical fluid from the organ bath, and a connection device(s) 64 for connecting the tubing to, for example, tubing 50c, 81, 82, 91 and/or 132, (see, for example, FIG. 4D) of an organ storage, transporter, perfusion and/or diagnostic apparatus.

Vent 61 preferably includes a filter device, and provides for control and/or equalization of pressure within and without the cassette without contamination of the contents of the cassette. For example, organs are frequently transported by aircraft, in which pressure changes are the norm. Even ground transportation can involve pressure changes as motor vehicles pass through tunnels, over mountains, etc. In addition, one or more lids 410 and 420 of cassette 65 can create an airtight seal with the cassette 65. This air tight seal can create a pressure difference between the inside and outside of cassette 65.

It is often desirable to provide for pressure equalization of the cassette under such circumstances. However, free flow of air to achieve pressure equalization might introduce contaminants into the cassette. Thus, a filtering vent 61 is preferably provided to allow the air flow without permitting introduction of contaminants into the cassette.

The filter preferably will let clean air pass in both directions but will not allow dirt, dust, liquids and other contaminants to pass. The pore size in the filters can be any size desired and can be small enough to prevent bacteria from passing.

A pressure control valve can optionally be associated with vent 61 as well. Such a valve may be configured or controlled to restrict the rate at which external pressure changes are transmitted to the inside of the cassette, or even to prevent pressure increases and/or decreases, as desired.

The cassette 65, and/or the organ support, opening(s), tubing(s) and/or connections(s), may be specifically tailored to the type of organ and/or size of organ to be perfused. Flanges 67c of the side support walls 67a can be used to support the cassette 65 disposed in an organ storage, transporter, perfusion and/or diagnostic apparatus. The cassette 65 may further include a handle 68 which allows the cassette 65 to be easily handled, as shown, for example, in FIGS. 4C and 4D. Each cassette 65 may also be provided with its own mechanism (e.g., stepping motor/cam valve 75 (for example, in the handle portion 68, as shown in FIG. 4C)) for fine tuning the pressure of medical fluid perfused into the organ 60 disposed therein, as discussed in more detail below. Alternatively, or in addition, pressure may, in embodiments, be controlled by way of a microprocessor, as shown in FIG. 3, which received pressure sensor data from pressure sensor P1.

Figure 6A:
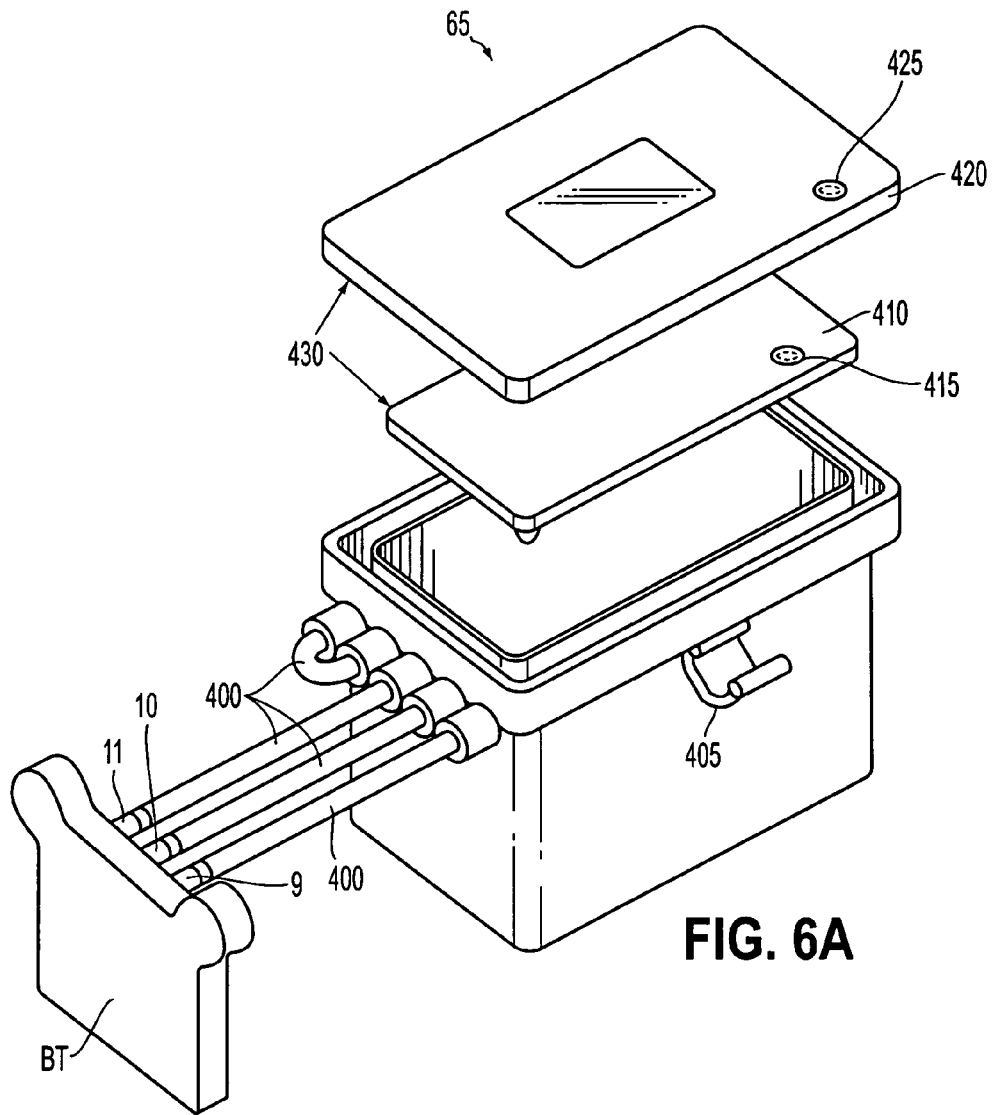
FIGS. 6A and 6B show an embodiment of an organ cassette of the present invention.
Figure 6B:
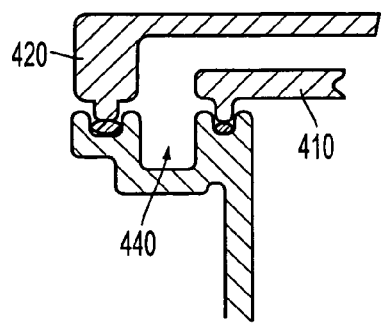

FIGS. 6A-6B show an alternative embodiment of cassette 65. In FIG. 6A, cassette 65 is shown with tubeset 400. Tubeset 400 can be connected to perfusion apparatus 1 or to an organ transporter or an organ diagnostic apparatus, and allows cassette 65 to be moved between various apparatus without jeopardizing the sterility of the interior of cassette 65. Preferably, cassette 65 is made of a sufficiently durable material that it can withstand penetration and harsh impact. Cassette 65 is provided with a lid, preferably two lids, an inner lid 410 and an outer lid 420. As shown in FIG. 6A, the tube set may be connected to a bubble trap device BT. A preferred such device is described in detail in a U.S. provisional patent application, Ser. No. 60/459,981, filed simultaneously herewith entitled "Device for separating bubbles from a liquid path".

The cassette 65 is a portable device. As such, one or more lids 410 and 420 can create a substantially airtight seal with the cassette 65. This air tight seal can create a pressure difference between the inside and outside of cassette 65. Pressure sensors that control perfusion of the organ may be referenced to the atmospheric pressure. In such embodiments, it is desirable that the air space around the organ in cassette 65 is maintained at atmospheric pressure. Accordingly, the cassette may also include one or more devices for controlling the pressure. The devices for controlling pressure can be active or passive devices such as valves or membranes. Membranes 415 and 425, for example, can be located in the inner lid 410 and outer lid 420, respectively. It should be appreciated that any number of membranes can be located in the cassette (including its lid(s)) without departing from the spirit and scope of the invention. The membranes 415 and 425 are preferably hydrophobic membranes which help maintain an equal pressure between the inside and the outside of the cassette. The membranes 415 and 425, if sufficiently flexible, can be impermeable or substantially impermeable. Alternatively, they may include filters that will let clean air pass in both directions, however, the membranes 415 and 425 will not allow dirt, dust, liquids and other contaminants to pass. The pore size in the filters can be any size desired, and preferably, the pore size of the membranes 415 and 425 can be small enough to prevent bacteria from passing. The actions of the membranes 415 and 425 and corresponding filters help maintain the sterility of the system.

Preferably, cassette 65 is made of a sufficiently durable material that it can withstand penetration and harsh impact. Cassette 65 is provided with a lid, preferably two lids, an inner lid 410 and an outer lid 420. The lids 410 and 420 may be removable or may be hinged or otherwise connected to the body of cassette 65. Clasp 405, for example, may provide a mechanism to secure lids 410 and 420 to the top of cassette 65. Clasp 405 may additionally be configured with a lock to provide further security and stability. A biopsy and/or venting port 430 may additionally be included in inner lid 410 or both inner lid 410 and outer lid 420. Port 430 may provide access to the organ to allow for additional diagnosis of the organ with minimal disturbance of the organ. Cassette 65 may also have an overflow trough 440 (shown in FIG. 6B as a channel present in the top of cassette 65). When lids 410 and 420 are secured on cassette 65, overflow trough 440 provides a region that is easy to check to determine if the inner seal is leaking. Perfusate may be poured into and out of cassette 65 and may be drained from cassette 65 through a stopcock or removable plug.

Cassette 65 and/or its lid(s) may be constructed of an optically transparent material to allow for viewing of the interior of cassette 65 and monitoring of the organ and to allow for video images or photographs to be taken of the organ. A perfusion apparatus or cassette 65 may be wired and fitted with a video camera or a photographic camera, digital or otherwise, to record the progress and status of the organ. Captured images may be made available over a computer network such as a local area network or the internet to provide for additional data analysis and remote monitoring. Cassette 65 may also be provided with a tag that would signal, e.g., through a bar code, magnetism, radio frequency, or other means, the location of the cassette, that the cassette is in the apparatus, and/or the identity of the organ to perfusion, storage, diagnostic and/or transport apparatus. Cassette 65 may be sterile packaged and/or may be packaged or sold as a single-use disposable cassette, such as in a peel-open pouch. A single-use package containing cassette 65 may also include tubeset 400 and/or tube frame 200, discussed further below.

Cassette 65 is preferably configured such that it may be removed from an organ perfusion apparatus and transported to another organ perfusion and/or diagnostic apparatus in a portable transporter apparatus as described herein or, for example, a conventional cooler or a portable container such as that disclosed in U.S. Pat. No. 6,209,343, or U.S. Pat. No. 5,586,438 to Fahy, both of which are hereby incorporated by reference in their entirety.

In various exemplary embodiments according to this invention, when transported, the organ may be disposed on the organ supporting surface 66 and the cassette 65 may be enclosed in a preferably sterile bag 69, as shown, for example, in FIG. 4A. When the organ is perfused with medical fluid, effluent medical fluid collects in the bag 69 to form an organ bath. Alternatively, cassette 65 can be formed with a fluid tight lower portion in which effluent medical fluid may collect, or effluent medical fluid may collect in another compartment of an organ storage, transporter, perfusion and/or diagnostic apparatus, to form an organ bath. In either case, the bag 69 would preferably be removed prior to inserting the cassette into an organ storage, transporter, perfusion and/or diagnostic apparatus. Further, where a plurality of organs are to be perfused, multiple organ compartments may be provided. Alternatively, cassette 65 can be transported in the cassette and additionally carried within a portable organ transporter.

Figure 7:
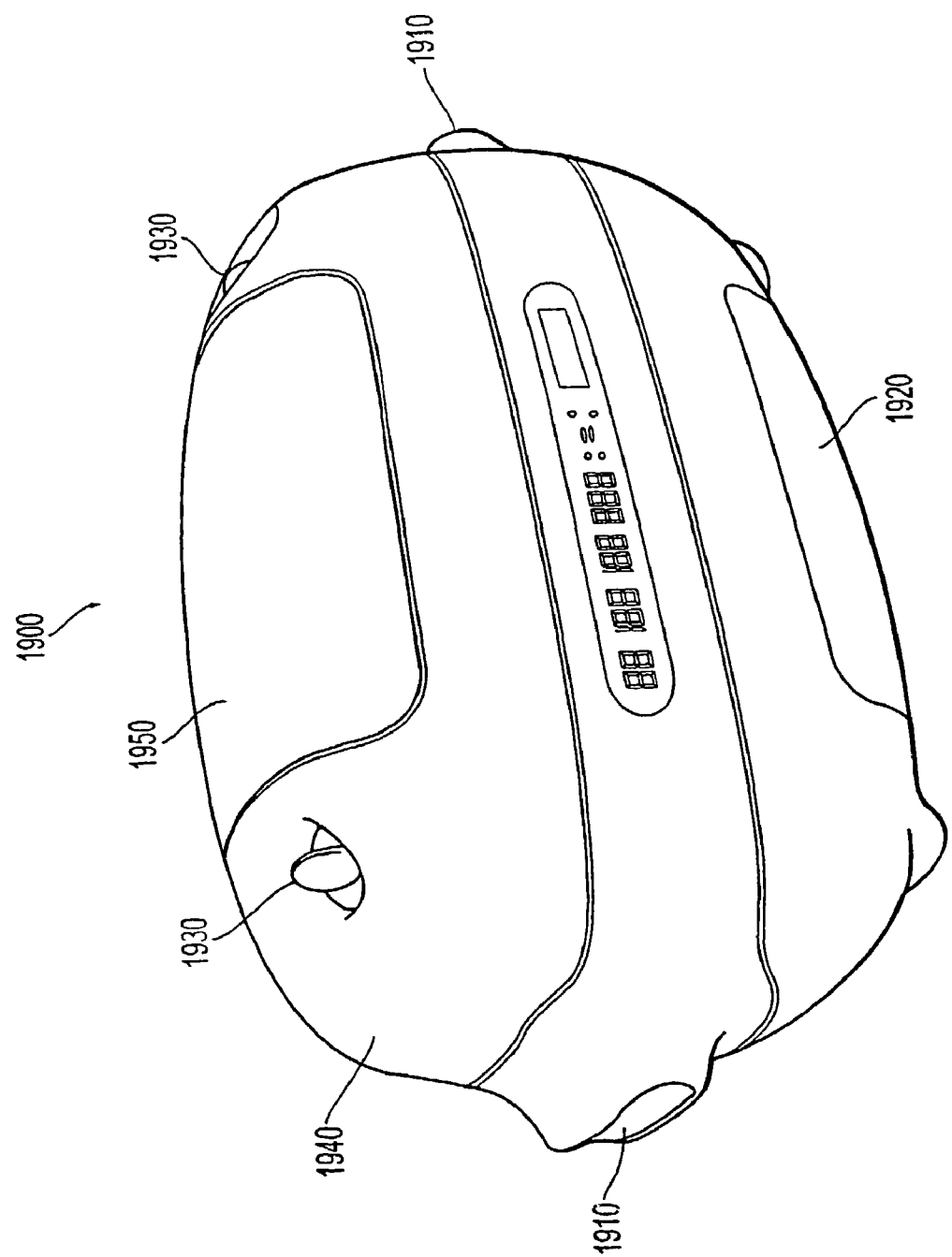
FIG. 7 shows an exterior perspective view of an organ transporter according to the present invention.

FIG. 7 shows an external view of an embodiment of a transporter 1900 of the invention. The transporter 1900 of FIG. 7 has a stable base to facilitate an upright position and handles 1910 for carrying transporter 1900. Transporter 1900 may also be fitted with a shoulder strap and/or wheels to assist in carrying transporter 1900. A control panel 1920 is preferably also provided. Control panel 1920 may display characteristics, such as, but not limited to, infusion pressure, attachment of the tube frame, power on/off, error or fault conditions, flow rate, flow resistance, infusion temperature, bath temperature, pumping time, battery charge, temperature profile (maximums and minimums), cover open or closed, history log or graph, and additional status details and messages, some or all of which are preferably further transmittable to a remote location for data storage and/or analysis. Flow and pressure sensors or transducers in transporter 1900 may be provided to calculate various organ characteristics including pump pressure and vascular resistance of an organ, which can be stored in computer memory to allow for analysis of, for example, vascular resistance history, as well as to detect faults in the apparatus, such as elevated pressure.

Transporter 1900 preferably has latches 1930 that require positive user action to open, thus avoiding the possibility that transporter 1900 inadvertently opens during transport. Latches 1930 hold top 1940 in place on transporter 1900 in FIG. 7. Top 1940 or a portion thereof may be constructed with an optically transparent material to provide for viewing of the cassette and organ perfusion status. Transporter 1900 may be configured with a cover open detector that monitors and displays whether the cover is open or closed. Transporter 1900 may be configured with an insulating exterior of various thicknesses to allow the user to configure or select transporter 1900 for varying extents and distances of transport. In embodiments, compartment 1950 may be provided to hold patient and organ data such as charts, testing supplies, additional batteries, hand-held computing devices and/or configured with means for displaying a UNOS label and/or identification and return shipping information.

Figure 8:
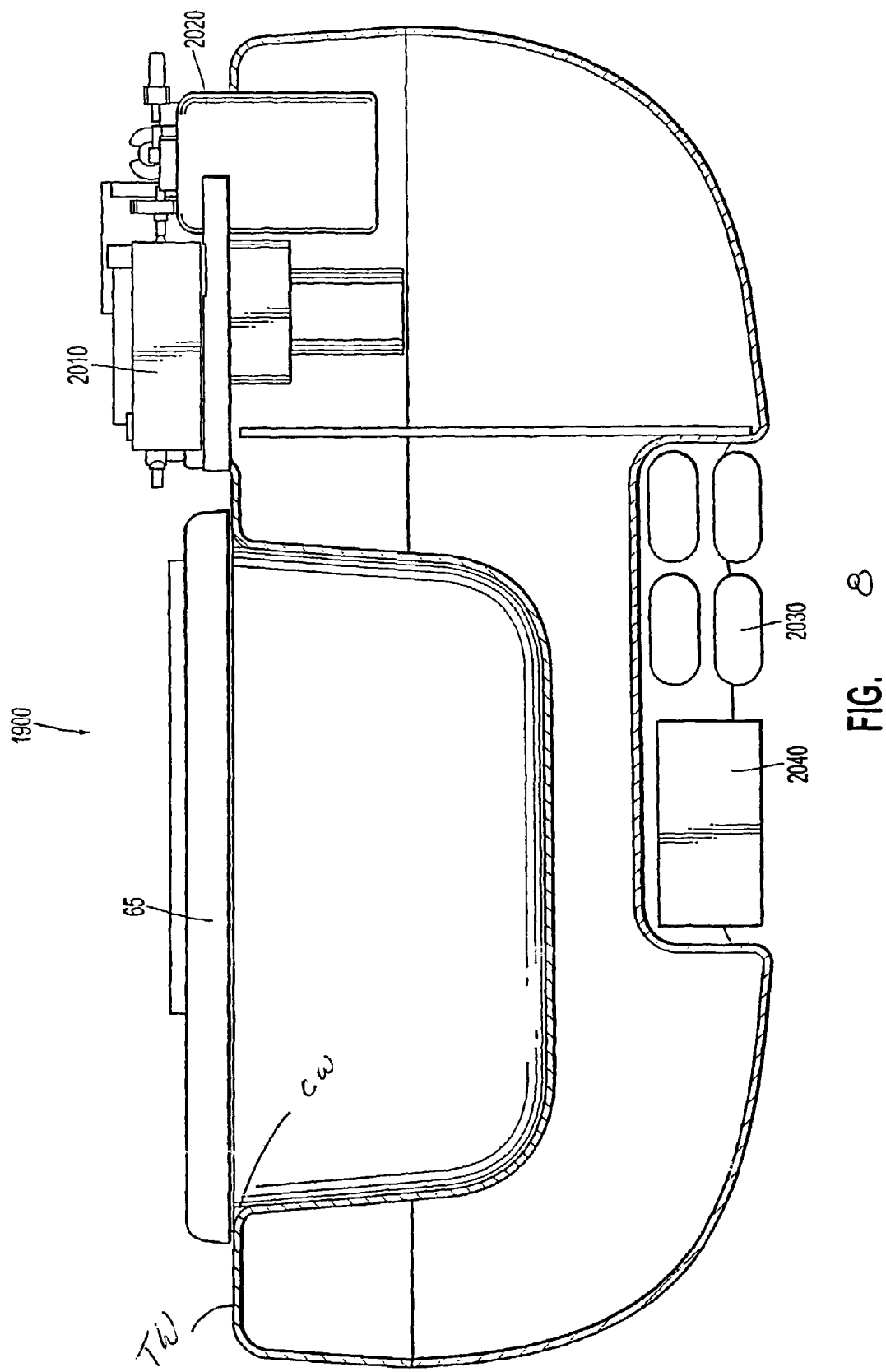
FIG. 8 shows a cross section view of an organ transporter of FIG. 7.

FIG. 8 shows a cross-section view of a transporter 1900. Transporter 1900 contains cassette 65 and pump 2010. Cassette 65 may preferably be placed into or taken out of transporter 1900 without disconnecting tubeset 400 from cassette 65, thus maintaining sterility of the organ. In embodiments, sensors in transporter 1900 can detect the presence of cassette 65 in transporter 1900, and depending on the sensor, can read the organ identity from a barcode or radio frequency or other "smart" tag that may be attached or integral to cassette 65. This can allow for automated identification and tracking of the organ and helps monitor and control the chain of custody. A global positioning system may be added to transporter 1900 and/or cassette 65 to facilitate tracking of the organ. Transporter 1900 may be interfaceable to a computer network by hardwire connection to a local area network or by wireless communication while in transit. This interface may allow data such as perfusion parameters, vascular resistance, and organ identification and transporter and cassette location to be tracked and displayed in real-time or captured for future analysis.

Transporter 1900 also preferably contains a filter 2020 to remove sediment and other particulate matter, preferably ranging in size from 0.05 to 15 microns in diameter or larger, from the perfusate to prevent clogging of the apparatus or the organ. Transporter 1900 preferably also contains batteries 2030, which may be located at the bottom of transporter 1900 or beneath pump 2010 or at any other location but preferably one that provides easy access to change batteries 2030. Batteries 2030 may be rechargeable outside of transporter 1900 or while within transporter 1900 and/or are preferably hot-swappable one at a time. Batteries 2030 are preferably rechargeable rapidly and without full discharge. Transporter 1900 may also provide an additional storage space 2040, for example, at the bottom of transporter 1900, for power cords, batteries and other accessories. Transporter 1900 may also include a power port for a DC hookup, e.g., to a vehicle such as an automobile or airplane, and/or for an AC hookup.

As shown in FIG. 8, the cassette wall CW is preferably configured to mate with a corresponding configuration of inner transporter wall TW to maximize contact, and thus heat transfer, therebetween as discussed in more detail below.

Figure 9:
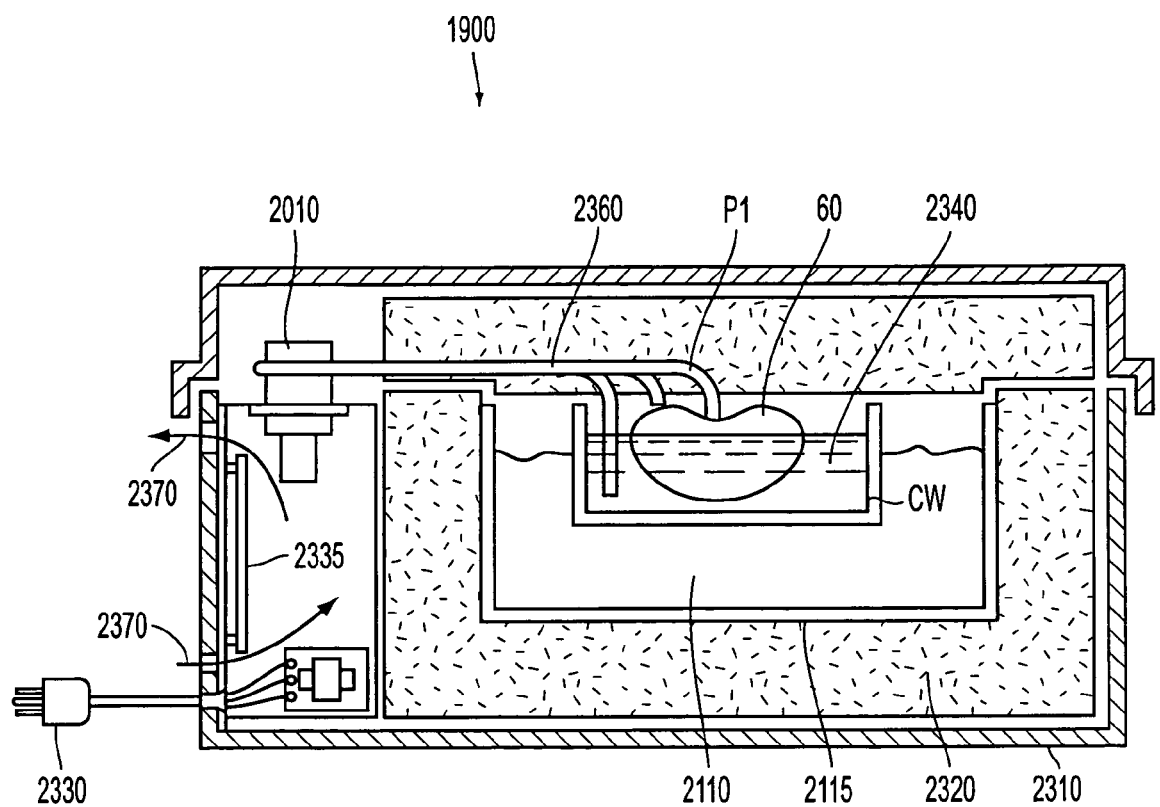
FIG. 9 shows an alternative cross-section view of an organ transporter of FIG. 7.

FIG. 9 shows an alternative cross-section of transporter 1900. In FIG. 9, the transporter 1900 may have an outer enclosure 2310 which may, for example, be constructed of metal, or preferably a plastic or synthetic resin that is sufficiently strong to withstand penetration and impact. Transporter 1900 contains insulation 2320, preferably a thermal insulation made of, for example, glass wool or expanded polystyrene. Insulation 2320 may be various thicknesses ranging from 0.5 inches to 5 inches thick or more, preferably 1 to 3 inches, such as approximately 2 inches thick. Transporter 1900 may be cooled by coolant 2110, which may be, e.g., an ice and water bath or a cryogenic material. In embodiments using cryogenic materials, the design should be such that organ freezing is prevented. An ice and water mixture is preferably an initial mixture of approximately 1 to 1, however, in embodiments the ice and water bath may be frozen solid. Transporter 1900 can be configured to hold various amounts of coolant, preferably up to 10 to 12 liters. An ice and water bath is preferable because it is inexpensive and generally can not get cold enough to freeze the organ. Coolant 2110 preferably lasts for a minimum of 6 to 12 hours and more preferably lasts for a minimum of 30 to 50 hours without changing coolant 2110. The level of coolant 2110 may, for example, be viewed through a transparent region of transporter 1900 or be automatically detected and monitored by a sensor. Coolant 2110 can preferably be replaced without stopping perfusion or removing cassette 65 from transporter 1900. Coolant 2110 is preferably maintained in a watertight compartment 2115 of transporter 1900. For example, an inner transporter wall TW as shown in FIG. 8 can be interposed between the coolant 2110 and cassette wall (CW) in the apparatus of FIG. 9. Compartment 2115 preferably prevents the loss of coolant 2110 in the event transporter 1900 is tipped or inverted. Heat is conducted from the walls of the perfusate reservoir/cassette 65 into coolant 2110 enabling control within the desired temperature range. Coolant 2110 is a fail-safe cooling mechanism because transporter 1900 automatically reverts to cold storage in the case of power loss or electrical or computer malfunction. Transporter 1900 may also be configured with a heater to raise the temperature of the perfusate.

Transporter 1900 may be powered by batteries or by electric power provided through plug 2330. An electronics module 2335 may also be provided in transporter 1900. Electronics module 2335 may be cooled by vented air convection 2370, and may further be cooled by a fan. Preferably, electronic module 2335 is positioned separate from the perfusion tubes to prevent the perfusate from wetting electronics module 2335 and to avoid adding extraneous heat from electronics module 2335 to the perfusate. Transporter 1900 preferably has a pump 2010 that provides pressure to perfusate tubing 2360 (e.g. of tube set 400) to deliver perfusate 2340 to organ 60. Pressure sensor P1 is provided on prefusate tubing 2360 to relay conditions therein to the microprocessor 150, shown in FIG. 3. Transporter 1900 may be used to perfuse various organs such as a kidney, heart, liver, small intestine and lung. Transporter 1900 and cassette 65 may accommodate various amounts to perfusate 2340, for example up to 3 to 5 liters. Preferably, approximately 1 liter of a hypothermic perfusate 2340 is used to perfuse organ 60.

Cassette 65 and transporter 1900 are preferably constructed to fit or mate such that efficient heat transfer is enabled. Preferably, the transporter 1900 contains a compartment 2115 for receiving the cassette. The transporter 1900 preferably relies on conduction to move heat from the cassette 65 to coolant 2110 contained in compartment 2115. This movement of heat allows the transporter 1900 to maintain a desired temperature of the perfusion solution. The geometric elements of cassette 65 and transporter 1900 are preferably constructed such that when cassette 65 is placed within transporter 1900, the contact area between cassette 65 and transporter 1900 is as large as possible and they are secured for transport.

Pump 2010, which may be a peristaltic pump, or any type of controllable pump, may be used to move fluid throughout the infusion circuit of, for example, the organ perfusion apparatus of FIG. 2, the organ cassette of FIG. 6a, and/or the organ transporter of FIG. 8, and into organ 60.

It should be appreciated that the organ 60 may be any type of organ, a kidney, liver, or pancreas, for example, and the organ may be from any species, e.g., human, cow, pig, etc.

Preferably, immediately preceding organ 60 lies pressure sensor P1, which can sense the pressure of fluid flow at the position before the fluid enters organ 60. As fluid is moved throughout the infusion circuit, organ 60 provides resistance. Pressure sensor P1 detects the pressure that the organ creates by its resistance as the fluid moves through it. At a position after organ 60, there is little pressure, as the fluid typically flows out of the organ freely and into an organ bath.

Figure 10:
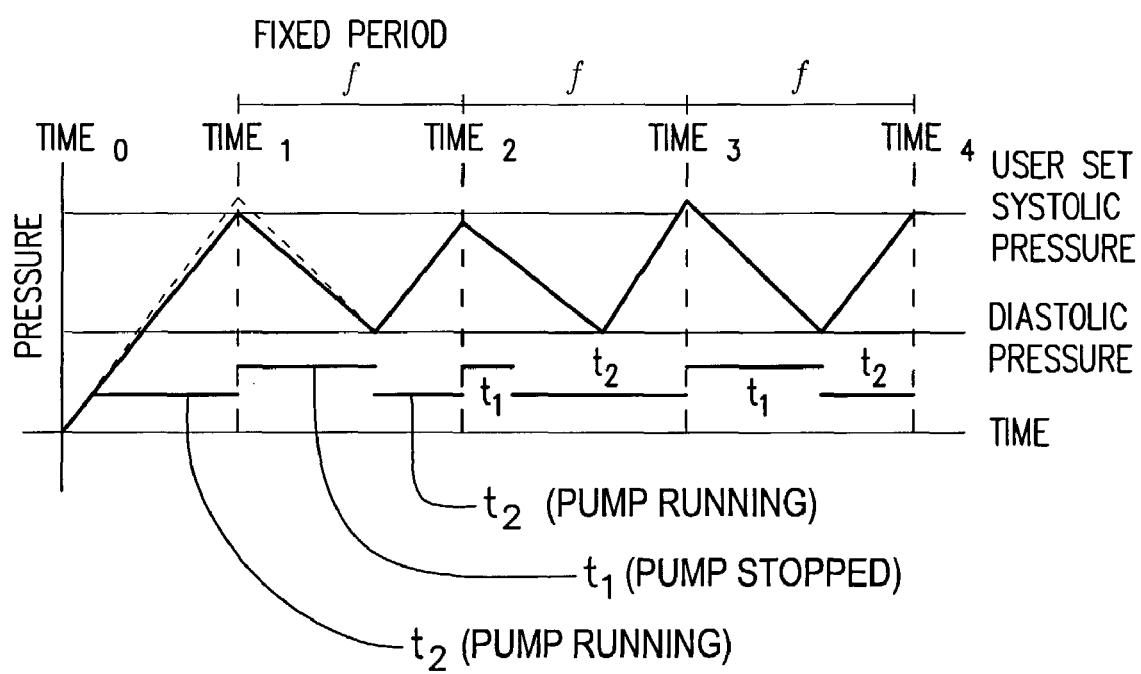
FIG. 10 is a pressure vs. time graph which shows the organ perfusion pressure and the pump state of the pump supplying the pressure at a given time for variable pump activation/inactivation periods.

FIG. 10 is a pressure vs. time graph which shows the organ perfusion pressure and the pump state of pump 2010 supplying the pressure at a given time for embodiments of the invention involving variable pump activation periods. A user or computer sets a desired systolic pressure, which is the pressure of the fluid flow before entering organ 60 at pressure sensor P1, as discussed above. A fixed time interval f is also set, which may be, for example, set to a frequency of a low 1 beat per minute, or a high 200 beats per minute. Typically, f is set to produce between 20 and 60 beats per minute. Preferably, f is set to produce thirty beats per minute, or one beat every two seconds. The interval f may be predetermined, or may be user defined, and may be an interval that produces any frequency desired by the user.

At $time_0$, pump 2010 is activated and pumps fluid at a fixed rate through the infusion circuit, increasing the pressure measured by pressure sensor P1 until the pressure reaches the inputted systolic pressure value at $time_1$. At this initial stage, pump 2010 preferably runs continuously from $time_0$ to $time_1$. The duration from $time_0$ to $time_1$, is variable depending on the organ being perfused and does not necessarily depend on the frequency or time interval f.

Once it is determined that the pressure at pressure sensor P1 has reached the inputted systolic pressure (as represented by the solid line parabolic spike peaking at the user set systolic pressure at $time_1$) or it is determined that the pressure at pressure sensor P1 has exceeded the inputted systolic pressure value (as represented by the dotted line parabolic spike peaking above the user set systolic pressure at $time_1$), pump 2010 is deactivated at $time_1$ for a time interval $t_1$. Accordingly, the pressure measured at pressure sensor P1 begins to fall. At a point in time between $time_1$ and $time_2$ when the diastolic pressure has been reached, pump 2010 is activated again until the fixed time interval f ends at $time_2$. Preferably, at a time typically halfway between $time_1$ and $time_2$, which is the time interval f/2, pump 2010 is activated. Here, between $time_1$ and $time_2$, $t_1 = t_2 = f/2$.

It should be appreciated that pump 2010 can be deactivated and reactivated during the interval f so that the desired systolic pressure may be reached. For example, according to an exemplary embodiment of the present invention, if, at $time_2$ the desired systolic pressure is not reached at the end of the fixed time interval f, i.e., the systolic pressure at $time_2$ is less than the user or computer defined systolic pressure, then pump 2010 is stopped for a shorter period of time as represented by the $t_1$ shown between $time_2$ and $time_3$. Accordingly, pump 2010 is then activated at an earlier time from the beginning of $time_2$ during the next fixed interval f between $time_2$, and $time_3$, so that the inputted systolic pressure may be reached, or at least more closely approximated at $time_3$. According to this exemplary embodiment, between $time_2$ and $time_3$, $t_1 < t_2$, which indicates that the pump is running for a longer time than it is inoperative.

According to another exemplary embodiment of this invention, if between $time_2$ and $time_3$, the systolic pressure is reached (not shown), then pump 2010 can be controlled to maintain the systolic pressure until the end of $time_3$.

According to another exemplary embodiment of this invention, if, at $time_3$, the systolic pressure is greater than the user's inputted systolic pressure value at the end of the fixed time period f, as represented by the parabolic spike at $time_1$ which exceeds the user or computer defined systolic pressure, then pump 2010 is deactivated longer during the next fixed period f starting at $time_3$ in order for the user or computer defined systolic pressure to be reached at $time_4$. According to this exemplary embodiment, between $time_3$ and $time_4$, $t_1 > t_2$, which indicates that the pump is stopped for a longer time than it is running.

As such, according to exemplary embodiments of this invention, $t_1$ (the time during which the pump is stopped) and $t_2$ (the time during which the pump is activated) may be constantly increasing and/or decreasing over various fixed periods f so that the diastolic pressure (a free variable controlled by the organ) is as low as possible.

The method according to the foregoing embodiments of the present invention constantly balances $t_1$ and $t_2$ such that the sum of $t_1$ and $t_2$ adds up to the fixed period f. This compensates for the fact that the organ resistance measured by pressure sensor P1 changes over time due to the shape altering characteristics of living tissue. Advantageously, embodiments of the present invention are able to overcome this varying resistive nature of living organs by constantly increasing and decreasing time intervals $t_1$ and $t_2$ over sequential fixed periods f so that a fluid may be introduced to the organ at a constant rate.

Figure 11:
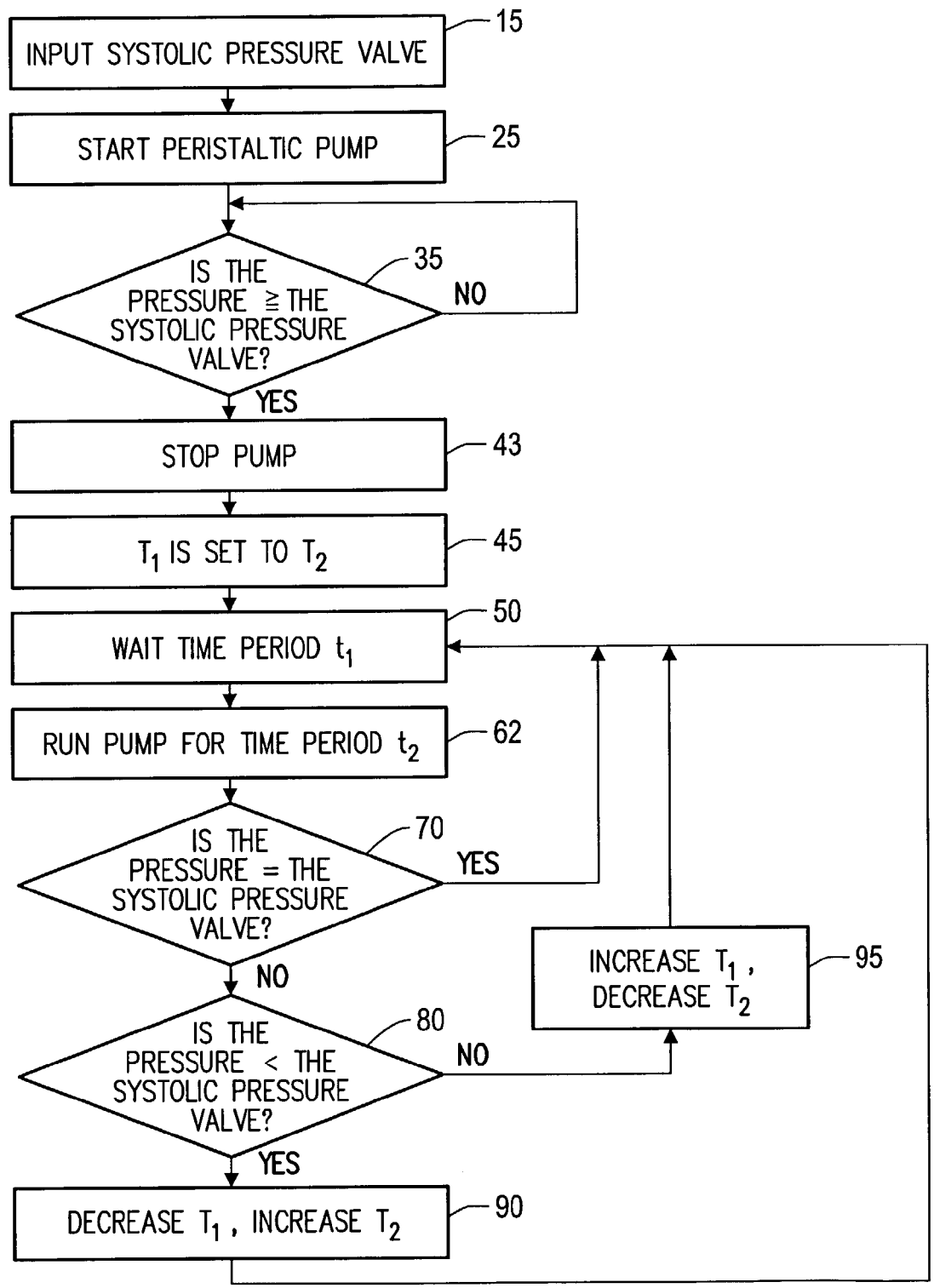
FIG. 11 is a flow diagram which shows the process flow of FIG. 10.

In FIG. 11, a user or computer enters a systolic pressure value at operation 15. A peristaltic pump, for example, or any other type of controllable pump, begins operation at operation 25. At operation 35, a pressure sensor, such as pressure sensor P1 checks to determine if the pressure as measured in front of organ 60 is greater than or equal to the systolic pressure value previously set by the user. If pressure is lower than the systolic pressure value, then operation 35 is repeated until it determines that the pressure is greater than or equal to the systolic pressure value. When this occurs, processing proceeds to operation 43.

At operation 43, pump 2010 may be stopped altogether, and processing proceeds to operation 45. At operation 45, $t_1$ and $t_2$ both are set equal to fixed period f/2, and processing proceeds to operation 50.

At operation 50, pump 2010 remains inactive for a time period $t_1$. When this time period is over, processing proceeds to operation 62. At operation 62, pump 2010 is started and remains running for a time period $t_2$. After time period $t_2$ has expired, and pump 2010 has stopped, processing proceeds to operation 70.

At operation 70, pressure sensor P1 is queried to determine whether the fluid flow pressure for organ 60 is equal to the set systolic pressure value. If the determined pressure is equal to the systolic pressure, then the values of $t_1$ and $t_2$ are the desired values for the current permeability of and resistance generated by organ 60. Accordingly, the values of $t_1$ and $t_2$ are not changed, and processing loops back to operation 50.

If, however, operation 70 determines that the pressure is not equal to the set systolic pressure value, then processing proceeds to operation 80.

At operation 80, pressure sensor P1 is queried to determine whether the fluid flow pressure is less than the systolic pressure value. If so, then processing proceeds to operation 90. If, however, the fluid flow pressure is not less than the user or computer defined systolic pressure value (i.e., the pressure is greater than the systolic pressure value), processing proceeds to operation 95.

At operation 90, the value of $t_1$ is decreased, and the value of $t_2$ is increased by a determined amount, which may be calculated by microprocessor 150 using the difference between the user or computer defined systolic pressure value and the actual systolic pressure at the end of a fixed frequency f. Processing loops back to operation 50.

At operation 95, the value of $t_1$ is increased, and the value of $t_2$ is decreased by a determined amount, which may be calculated by microprocessor 150 using the difference between the user or computer defined systolic pressure value and the actual systolic pressure at the end of a fixed frequency f, and processing loops back to operation 50.

Figure 12:
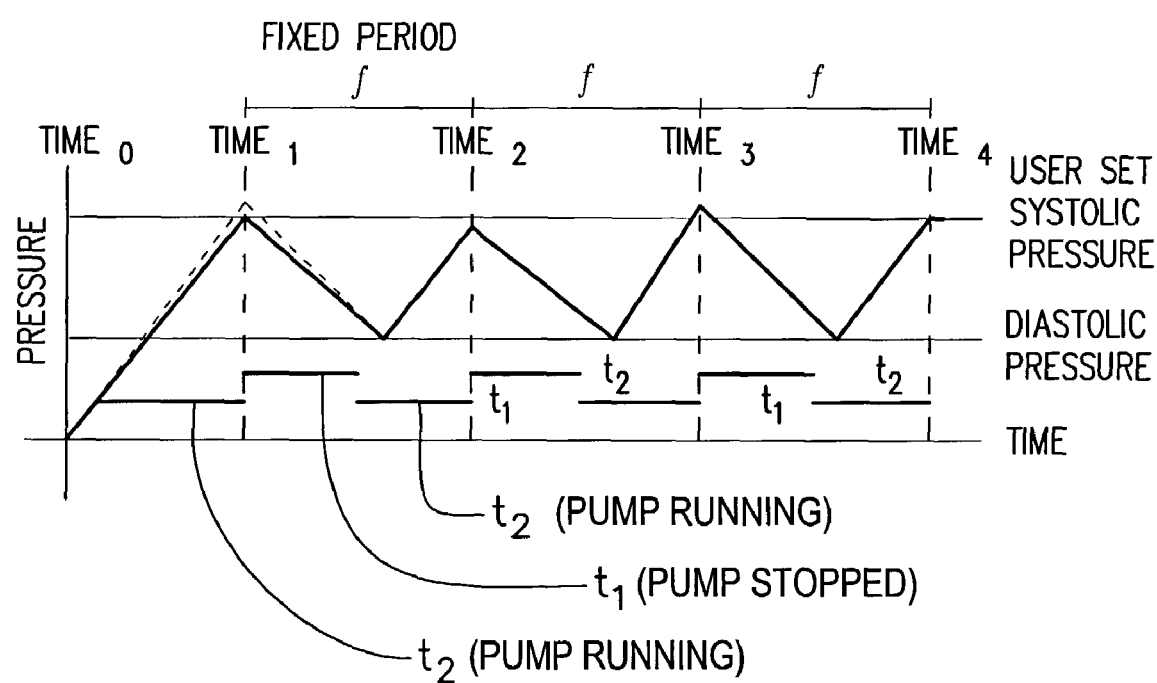
FIG. 12 is a pressure vs. time graph which shows the organ perfusion pressure and the pump state of the pump supplying the pressure at a given time for static pump activation/inactivation periods.

In alternative embodiments illustrated by FIG. 12, $t_1$ and $t_2$ are equal throughout all time intervals f, so that pump 2010 is activated for half of every fixed interval f, and deactivated for the other half of fixed interval f. The duty cycle of the motor utilized in pump 2010 is increased and decreased over time to achieve the desired systolic pressure value.

For example, according to various exemplary embodiments of FIG. 12, before $time_0$, pump 2010 is inoperative. A user or computer sets a desired systolic pressure, which is the pressure of the fluid flow before entering organ 60 at pressure sensor P1, as discussed above. A fixed interval f is also set as discussed above.

At $time_0$, pump 2010 is activated at a specific duty cycle, and pumps fluid using this initial duty cycle through the infusion circuit, increasing the pressure measured by pressure sensor P1 until the pressure reaches the inputted systolic pressure value at $time_1$. At this initial stage, between $time_0$ and $time_1$, pump 2010 may run continuously as represented by $t_2=time_1-time_0$.

Once pressure at pressure sensor P1 detects the inputted systolic pressure (as represented by the solid line parabolic spike peaking at the user set systolic pressure at $time_1$) or the pressure at pressure sensor P1 has exceeded the inputted systolic pressure value (as represented by the dotted line parabolic spike peaking above the user set systolic pressure at $time_1$), pump 2010 is deactivated at $time_1$, for a time interval $t_1$. Accordingly, the pressure measured at pressure sensor P1 begins to fall. At a point in time between $time_1$ and $time_2$ pump 2010 is activated again until the fixed period frequency f ends at $time_2$. Preferably, at a time halfway between $time_1$ and $time_2$, which is the time interval f/2, pump 2010 is activated. Here, between $time_1$ and $time_2$, as with all fixed periods f in this embodiment, $t_1$ and $t_2$ are constant. In this embodiment, $t_1=t_2=f/2$; however, it should be appreciated that in other embodiments $t_1$ and $t_2$ do not have be equal.

It should be appreciated that the duty cycle of pump 2010 may be increased or decreased during time interval f so that the desired systolic pressure may be reached. For example, according to an exemplary embodiment of this invention, if, at $time_2$ the systolic pressure is not reached at the end of the fixed time period f, i.e., the systolic pressure at $time_2$ is less than the user or computer defined systolic pressure, then the duty cycle of pump 2010 is increased during the next fixed period f so that the inputted systolic pressure may be reached, or at least more closely approximated at $time_3$. According to this exemplary embodiment, between $time_2$ and $time_3$, $t_1=t_2$, but the duty cycle of pump 2010 has been increased over that of the duty cycle of the pump between $time_1$ and $time_2$.

According to another exemplary embodiment of this invention, if, at $time_3$, the systolic pressure is greater than the user's inputted systolic pressure value at the end of the fixed time period f, as represented by the parabolic spike exceeding the user or computer defined systolic pressure, then pump 2010 is activated with a lower duty cycle during the next fixed period f starting at $time_3$ so that the inputted systolic pressure may be reached at $time_4$.

According to this exemplary embodiment, between $time_3$ and $time_4$, $t_1=t_2$, but the duty cycle of pump P1 has been decreased as compared to that of the duty cycle of the pump between $time_2$ and $time_3$.

As such, according to exemplary embodiments of this invention, the duty cycle of pump 2010 may be constantly increasing and/or decreasing over various fixed periods f so that the diastolic pressure (a free variable controlled by the organ) is as low as possible.

The method according to the above embodiments of the present invention controls a pump duty cycle such that it takes a time period $t_2$ to rise from the diastolic pressure to the systolic pressure This compensates for the fact that the organ resistance measured by pressure sensor P1 changes over time due to the shape altering characteristics of living tissue. Advantageously, embodiments of the present invention are able to overcome this varying resistive nature of living organs by constantly increasing and decreasing the duty cycle of pump 2010 over sequential fixed periods f.

Figure 13:
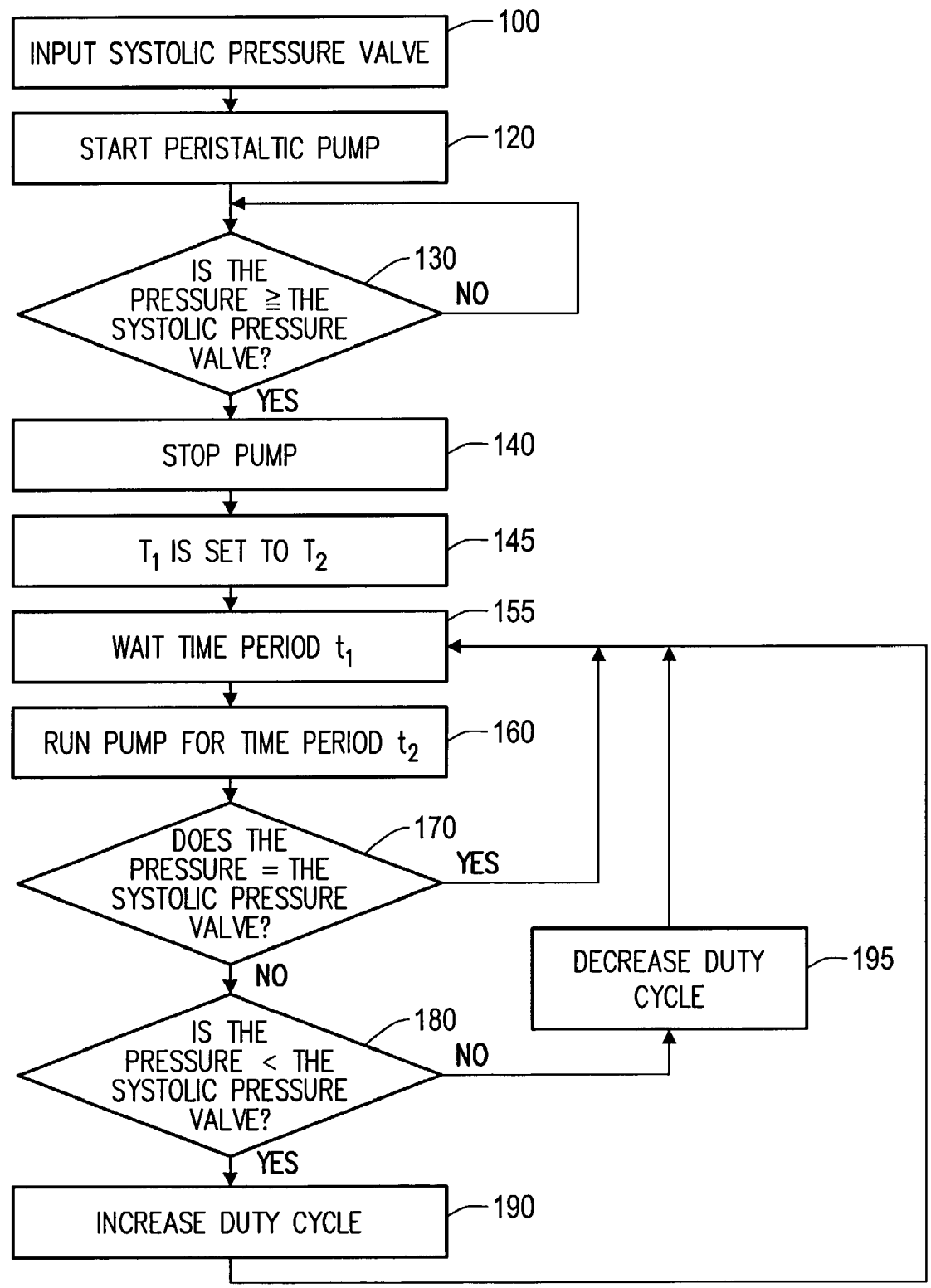
FIG. 13 is a flow diagram which shows the process flow of FIG. 12.

In FIG. 13, a user or computer enters a systolic pressure value at operation 100. A peristaltic pump, for example, or any other type of controllable pump, begins operation at operation 120. At operation 130, a pressure sensor, such as pressure sensor P1 checks to determine if the pressure as measured in front of organ 60 is greater than or equal to the systolic pressure value previously set by the user. If the sensed pressure is lower than the systolic pressure value, then operation 130 is repeated until the sensed pressure is greater than or equal to the systolic pressure value. When this occurs, processing proceeds to operation 140.

At operation 140, pump 2010 is preferably stopped altogether, and processing proceeds to operation 145. At operation 145 (or initially if desired), $t_1$ and $t_2$ both are set equal to fixed period f/2, and an initial duty cycle is determined for pump 2010 which may be calculated by microprocessor 150 using the difference between the user or computer defined systolic pressure value and the actual systolic pressure at the end of a fixed interval f, and processing proceeds to operation 155.

At operation 155, pump 2010 remains inactive for a time period $t_1$. When this time period is over, processing proceeds to operation 160. At operation 160, pump 2010 is started and remains running for a time period $t_2$. When time period $t_2$ has expired, pump 2010 stops, and processing proceeds to operation 170.

At operation 170, pressure sensor P1 is queried to determine whether the fluid flow pressure for organ 60 is equal to the set systolic pressure value. If the determined pressure is equal to the systolic pressure, then the current duty cycle of pump 2010 is the desired duty cycle for the current permeability of and resistance generated by organ 60; hence, the duty cycle of pump 2010 is not changed, and processing loops back to operation 155.

If, however, operation 170 determines that the pressure is not equal to the set systolic pressure value, then processing proceeds to operation 180.

At operation 180, pressure sensor P1 is queried to determine whether the fluid pressure is less than the systolic pressure value. If so, then processing proceeds to operation 190. If, however, the fluid pressure is not less than the user or computer defined systolic pressure value (i.e., the pressure is greater that the systolic pressure value), processing proceeds to operation 195.

At operation 190, the duty cycle is increased by a determined amount, which may be calculated by microprocessor 150 using the difference between the user or computer defined systolic pressure value and the actual systolic pressure at the end of a fixed interval f, so that during the next interval f a pressure closer to the set systolic pressure may be obtained. Processing next returns to operation 155.

At operation 195, the duty cycle is decreased by a determined amount, which may be calculated by microprocessor 150 using the difference between the user or computer defined systolic pressure value and the actual systolic pressure at the end of a fixed interval f, so that during the next interval f a pressure closer to the set systolic pressure may be obtained, and processing returns to operation 155.

While the invention has been described in conjunction with specific embodiments thereof, it is evident that many alternatives, modifications and variations may be apparent to those skilled in the art. Accordingly, the embodiments of the invention as set forth herein are intended to be illustrative, not limiting. Various changes may be made without departing from the spirit and scope of the invention.

What is claimed is:

1. A computer-executable method for controlling a pump for delivery of a liquid to an organ or tissue over a repeated series of fixed-length time intervals f, each interval f comprising a time $t_1$ and a time $t_2$ wherein $t_1+t_2$ equals the length of interval f, the method comprising:
   a) allowing output pressure of the pump to decrease over time $t_1$,
   b) increasing output pressure of the pump over time $t_2$,
   c) comparing achieved pump output pressure to a predetermined pressure at about the end of interval f,
   d) determining, based on the comparison between the achieved pump output pressure and the predetermined pressure, whether it is necessary to (i) adjust $t_1$ and $t_2$, (ii) adjust a rate of change of the output pressure during at least one of $t_1$ and $t_2$, or both (i) and (ii) so that the predetermined pressure is approximated by the output pressure at the end of next interval f, and
   e) at least one of (i) adjusting $t_1$ and $t_2$ if necessary so that the predetermined pressure is approximated by the output pressure at the end of the next interval f, and (ii) adjusting a rate of change of the output pressure during at least one of $t_1$ and $t_2$ if necessary so that the predetermined pressure is approximated by the output pressure at the end of the next interval f based on the determination of the step (d).

2. The method of claim 1, wherein step (a) comprises not running the pump for time $t_1$, step (b) comprises running the pump for time $t_2$, and step (d) comprises adjusting $t_1$ and $t_2$ so that the predetermined pressure is more closely approximated by the output pressure at the end of the next interval f.

3. The method of claim 1, wherein step (a) comprises reducing a duty cycle of the pump, step (b) comprises increasing a duty cycle of the pump, and step (d) comprises adjusting the rate of change of the output pressure during at least one of $t_1$ and $t_2$ to prevent the achieved pressure from substantially exceeding the predetermined pressure during the current interval f and the next interval f.

4. The method of claim 1, wherein step (a) comprises deactivating the pump, step (b) comprises running the pump, and step (d) comprises adjusting the rate of change of the output pressure during at least one of $t_1$ and $t_2$ to prevent the achieved pressure from substantially exceeding the predetermined pressure during the current interval f and the next interval f.

5. The method of claim 4, wherein step (d) comprises adjusting a duty cycle of the pump during time $t_2$ to prevent the achieved pressure from substantially exceeding the predetermined pressure during the current interval f and the next interval f.

6. The method of claim 3, wherein $t_1=t_2$.

7. The method of claim 1, further comprising comparing achieved pressure to a predetermined pressure at least one additional time during time $t_2$, and controlling a duty cycle of the pump to avoid allowing the achieved pressure to exceed the predetermined pressure before the end of said time $t_2$.

8. The method of claim 7, further comprising maintaining the achieved pressure at approximately the predetermined pressure until the end of said time $t_2$ when the achieved pressure reaches the predetermined pressure before the end of said time $t_2$.

9. The method of claim 1, comprising delivering said liquid to a kidney with said pump.

10. The method of claim 1, wherein the pump is a peristaltic pump.

11. The method of claim 1, wherein the achieved pump output pressure is determined at a location just upstream of an entrance of the liquid into the organ or tissue.

12. The method of claim 1, wherein the method is used to control a pump connected to an organ perfusion and storage device.

13. The method of claim 1, wherein the method is used to control a pump connected to an cassette that is transferable between an organ perfusion and storage device and an organ transport device.

14. The method of claim 1, wherein the method is used to control a pump connected to an organ transport device.

15. The method of claim 2, wherein $t_1$ and $t_2$ are adjusted by a microprocessor.

16. The method of claim 1, further comprising setting the length of said fixed-length time intervals f.

17. The method of claim 1, further comprising setting said predetermined pressure.

18. An apparatus for controlling a pump for delivery of a liquid to an organ or tissue over a repeated series of fixed-length time intervals f, each interval f comprising a time $t_1$ and a time $t_2$ wherein $t_1+t_2$ equals the length of interval f, the apparatus having a microprocessor, the apparatus comprising:
   a) a controller configured to allow output pressure of the pump to decrease over the time $t_1$,
   b) a controller configured to increase output pressure of the pump over the time $t_2$,
   c) a controller configured to compare achieved pump output pressure to a predetermined pressure at about the end of interval f,
   d) a controller configured to determine, based on the comparison between the achieved pump output pressure and the predetermined pressure, whether it is necessary to (i) adjust $t_1$ and $t_2$, (ii) adjust a rate of change of the output pressure during at least one of $t_1$ and $t_2$, or both (i) and (ii) so that the predetermined pressure is approximated by the output pressure at the end of next interval f, and
   e) a controller configured to perform at least one of (i) adjusting $t_1$ and $t_2$ if necessary so that the predetermined pressure is approximated by the output pressure at the end of the next interval f, and (ii) adjusting a rate of change of the output pressure during at least one of $t_1$ and $t_2$ if necessary so that the predetermined pressure is approximated by the output pressure at the end of the next interval f based on the determination of the controller (d).

19. An apparatus for controlling a pump for delivery of a liquid to an organ or tissue over a repeated series of fixed-length time intervals f, each interval f comprising a time $t_1$ and a time $t_2$ wherein $t_1+t_2$ equals the length of interval f, the apparatus having a microprocessor programmed with at least the following instructions:
   a) to allow output pressure of the pump to decrease over time $t_1$,
   b) to increase output pressure of the pump over time $t_2$,
   C) to compare achieved pump output pressure to a predetermined pressure at about the end of interval f,
   d) to determine, based on the comparison between the achieved pump output pressure and the predetermined pressure, whether it is necessary to (i) adjust $t_1$ and $t_2$, (ii) adjust a rate of change of the output pressure during at least one of $t_1$ and $t_2$, or both (i) and (ii) so that the predetermined pressure is approximated by the output pressure at the end of next interval f, and e) to at least one of (i) adjust $t_1$ and $t_2$ if necessary so that the predetermined pressure is approximated by the output pressure at the end of the next interval f, and (ii) adjust a rate of change of the output pressure during at least one of $t_1$ and $t_2$ if necessary so that the predetermined pressure is approximated by the output pressure at the end of the next interval f based on the determination of the instruction (d).

20. The apparatus of claim 19, further comprising said pump.

21. The apparatus of claim 20, further comprising an organ perfusion and storage device or an organ transport device, wherein said pump is connected to said organ perfusion and storage device or said organ transport device.

22. The apparatus of claim 20, further comprising a cassette that is transferable between an organ perfusion and storage device and an organ transport device, wherein said pump is connected to said cassette.

23. The apparatus of claim 20, wherein said pump is a peristaltic pump.

24. The apparatus of claim 19, wherein said microprocessor is pre-programmed with at least one said length of said time interval and predetermined pressure for a given organ type.

25. The apparatus of claim 19, further comprising an input device for setting or selecting the length of said time interval f.

26. The apparatus of claim 19, further comprising an input device for setting or selecting said predetermined pressure.

27. The apparatus of claim 18, wherein the controller (a) decreases the pressure and the controller (b) increases the pressure by activating and deactivating the pump, respectively.

28. The apparatus of claim 19, wherein the instruction (a) to decrease the pressure and the instruction (b) to increase the pressure is performed by activating and deactivating the pump, respectively.

29. An apparatus for controlling a pump for delivery of a liquid to an organ or tissue over a repeated series of fixed-length time intervals f, each interval f comprising a time $t_1$ and a time $t_2$ wherein $t_1+t_2$ equals the length of interval f, the apparatus having a microprocessor, the apparatus comprising:

a) means for allowing output pressure of the pump to decrease over the time $t_1$, b) means for increasing output pressure of the pump over the time $t_2$, c) means for comparing achieved pump output pressure to a predetermined pressure at about the end of interval f, d) means for determining, based on the comparison between the achieved pump output pressure and the predetermined pressure, whether it is necessary to (i) adjust $t_1$ and $t_2$, (ii) adjust a rate of change of the output pressure during at least one of $t_1$ and $t_2$, or both (i) and (ii) so that the predetermined pressure is approximated by the output pressure at the end of next interval f, and e) means for performing at least one of (i) adjusting $t_1$ and $t_2$ if necessary so that the predetermined pressure is approximated by the output pressure at the end of the next interval f, and (ii) adjusting a rate of change of the output pressure during at least one of $t_1$ and $t_2$ if necessary so that the predetermined pressure is approximated by the output pressure at the end of the next interval f based on the means for determining (d).

* * * * *